United States Patent [19]
Mahurkar

[11] Patent Number: 6,156,013
[45] Date of Patent: Dec. 5, 2000

[54] SAFETY SYRINGE

[76] Inventor: Sakharam D. Mahurkar, 6171 N. Sheridan Rd., Suite 1112, Chicago, Ill. 60660

[21] Appl. No.: 09/187,316

[22] Filed: Nov. 4, 1998

[51] Int. Cl.[7] .................................................. A61M 5/32
[52] U.S. Cl. ........................... 604/195; 604/198; 604/218
[58] Field of Search ................................... 604/195, 198, 604/218, 187, 110

[56] References Cited

U.S. PATENT DOCUMENTS

| | | | |
|---|---|---|---|
| D. 272,651 | 2/1984 | Mahurkar | D24/54 |
| 4,134,402 | 1/1979 | Mahurkar | 128/214 |
| 4,443,333 | 4/1984 | Mahurkar | 210/87 |
| 4,568,329 | 2/1986 | Mahurkar | 604/43 |
| 4,583,968 | 4/1986 | Mahurkar | 604/43 |
| 4,623,327 | 11/1986 | Mahurkar | 604/4 |
| 4,692,141 | 9/1987 | Mahurkar | 604/43 |
| 4,747,831 | 5/1988 | Kulli | 604/110 |
| 4,770,652 | 9/1988 | Mahurkar | 604/4 |
| 4,808,155 | 2/1989 | Mahurkar | 604/43 |
| 4,842,582 | 6/1989 | Mahurkar | 604/43 |
| 4,874,382 | 10/1989 | Lindemann et al. | 604/195 |
| 4,895,561 | 1/1990 | Mahurkar | 604/43 |
| 4,900,307 | 2/1990 | Kulli | 604/195 |
| 4,929,237 | 5/1990 | Medway | 604/198 |
| 4,978,343 | 12/1990 | Deysarz et al. | 604/195 |
| 4,986,813 | 1/1991 | Blake, III et al. | 604/110 |
| 5,019,044 | 5/1991 | Tsao | 604/110 |
| 5,084,029 | 1/1992 | Tagliaferri et al. | 604/195 |
| 5,112,316 | 5/1992 | Venturini | 604/195 |
| 5,116,319 | 5/1992 | ven den Haak | 604/195 |
| 5,147,303 | 9/1992 | Martin | 604/110 |
| 5,188,613 | 2/1993 | Shaw | 604/195 |
| 5,190,526 | 3/1993 | Murray et al. | 604/110 |
| 5,197,951 | 3/1993 | Mahurkar | 604/283 |
| 5,221,255 | 6/1993 | Mahurkar et al. | 604/43 |
| 5,221,256 | 6/1993 | Mahurkar | 604/43 |
| 5,273,541 | 12/1993 | Malencheck | 604/110 |
| 5,324,265 | 6/1994 | Murray et al. | 604/110 |
| 5,330,440 | 7/1994 | Stanners et al. | 604/195 |
| 5,338,311 | 8/1994 | Mahurkar | 604/195 |
| 5,342,308 | 8/1994 | Boschetti | 604/110 |
| 5,374,245 | 12/1994 | Mahurkar | 604/43 |
| 5,378,230 | 1/1995 | Mahurkar | 604/43 |
| 5,380,296 | 1/1995 | Smedley et al. | 604/193 |
| 5,395,337 | 3/1995 | Clemens et al. | 604/110 |
| 5,486,159 | 1/1996 | Mahurkar | 604/4 |
| 5,514,100 | 5/1996 | Mahurkar | 604/195 |
| 5,562,624 | 10/1996 | Righi et al. | 604/110 |
| 5,562,626 | 10/1996 | Sanpietro | 604/110 |
| 5,613,952 | 3/1997 | Pressly, Sr. et al. | 604/110 |
| 5,643,222 | 7/1997 | Mahurkar | 604/195 |
| 5,685,862 | 11/1997 | Mahurkar | 604/194 |
| 5,695,475 | 12/1997 | Best, Jr. et al. | 604/198 |

FOREIGN PATENT DOCUMENTS

| | | |
|---|---|---|
| 0566882 A1 | 10/1993 | European Pat. Off. . |
| 0677298 A1 | 10/1995 | European Pat. Off. . |
| WO 91/11212 | 8/1991 | WIPO . |
| WO 95/30445 | 11/1995 | WIPO . |
| WO 96/05879 | 2/1996 | WIPO . |

*Primary Examiner*—John D. Yasko
*Attorney, Agent, or Firm*—Jenkens & Gilchrist; Stephen G. Rudisill

[57] ABSTRACT

A single-use safety syringe assembly comprises an elongated, generally cylindrical barrel which forms a hollow nozzle located at the distal end of the barrel and which opens into the interior of the barrel. A plunger is slidably mounted in the barrel and forms a longitudinal cavity. A needle holder carries a hollow needle on its distal end, and the needle holder is slidably mounted in the longitudinal cavity of the plunger. A biasing arrangement urges the needle holder in a direction for retracting the needle into the barrel. However, a releasable latching arrangement retains the needle holder against the urging of the biasing arrangement in a position wherein the needle projects from the barrel. An In-Barrel assembly sequence is provided which permits sequentially inserting components of the syringe into the barrel and effecting assembly with a push of the plunger. An OTN catheter may also be employed in combination with the syringe assembly.

84 Claims, 15 Drawing Sheets

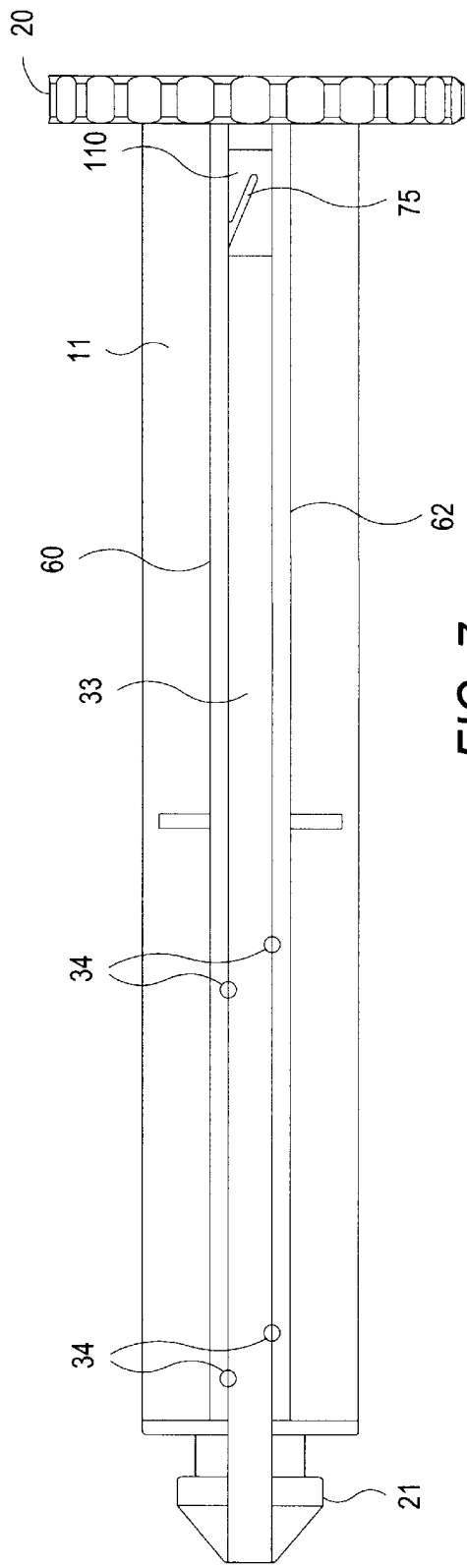
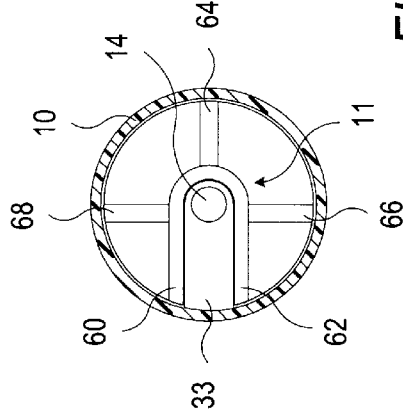
FIG. 9
FIG. 7
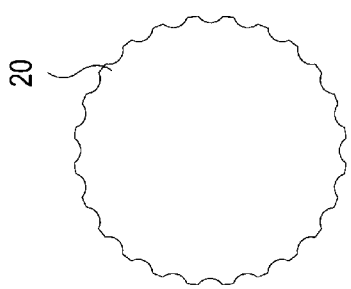
FIG. 8

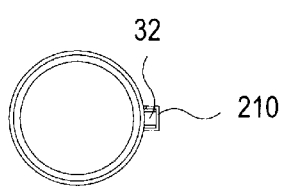
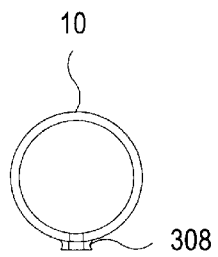
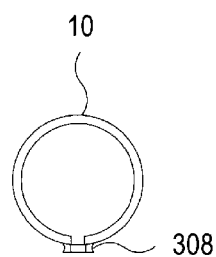
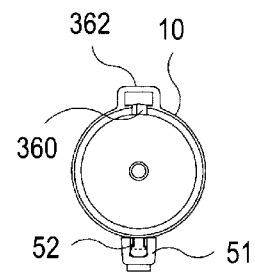
FIG. 11  FIG. 13  FIG. 15  FIG. 17
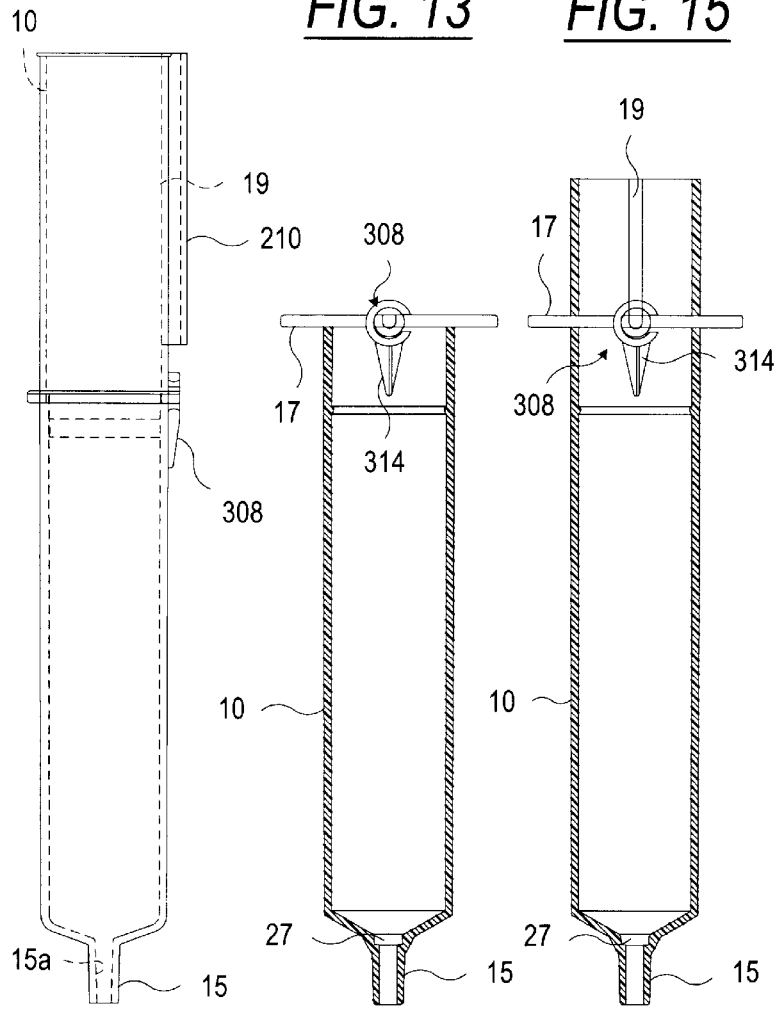
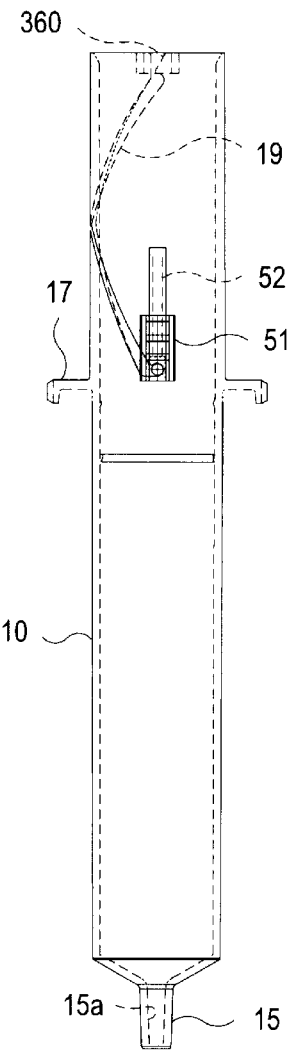
FIG. 10  FIG. 12  FIG. 14  FIG. 16

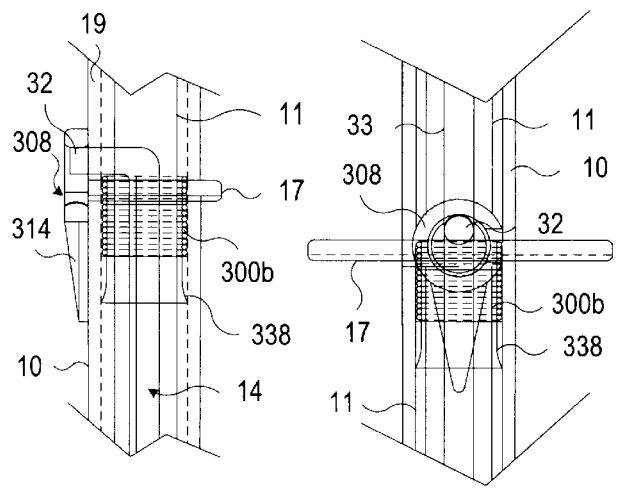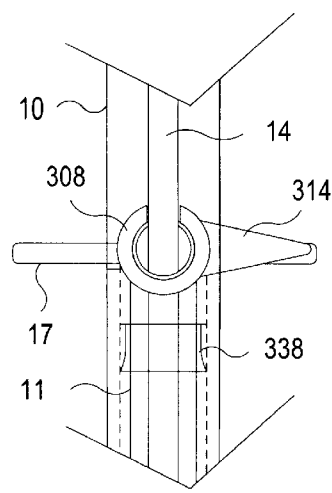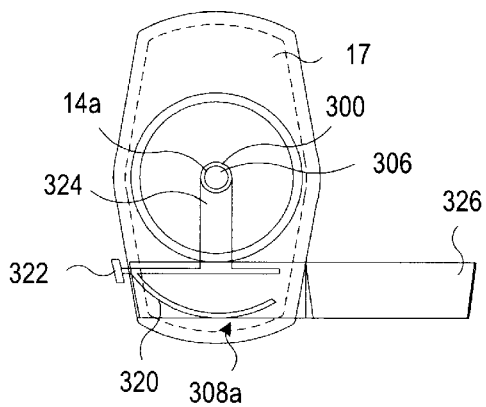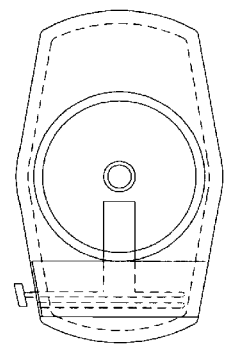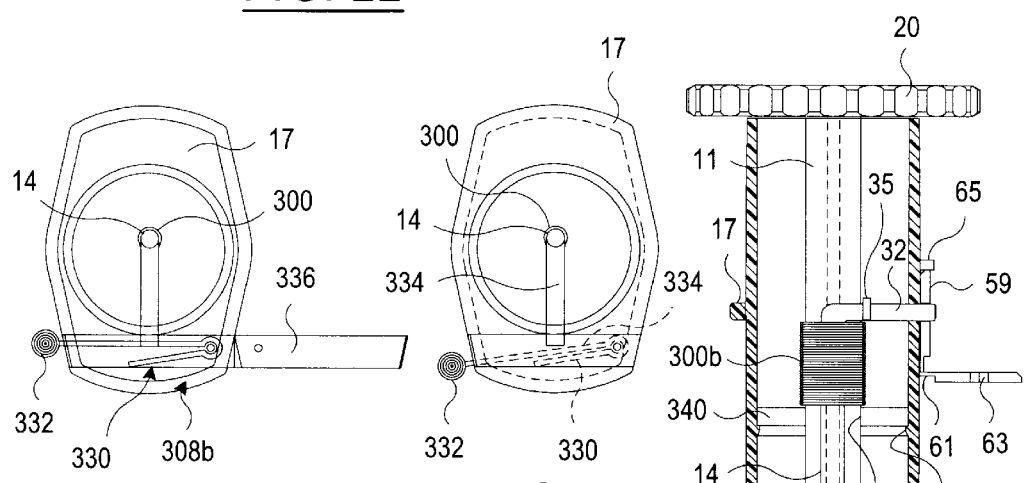
FIG. 19  FIG. 20  FIG. 21  FIG. 22  FIG. 23  FIG. 24  FIG. 25  FIG. 26

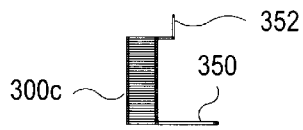
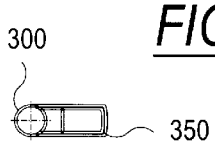
FIG. 27
FIG. 28
FIG. 31
FIG. 30
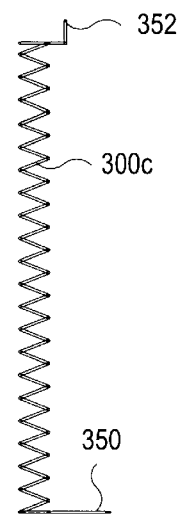
FIG. 29
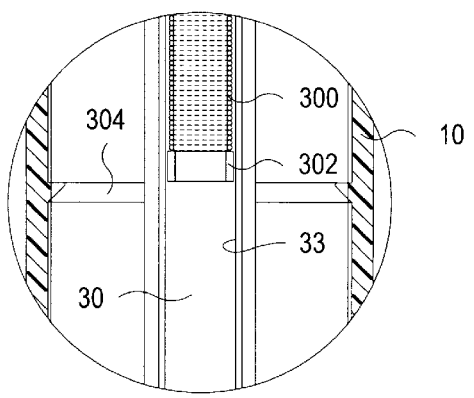
FIG. 33
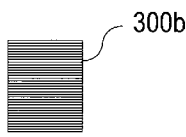
FIG. 32a
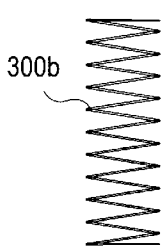
FIG. 32b
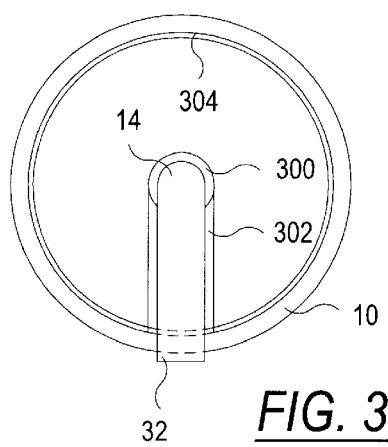
FIG. 34
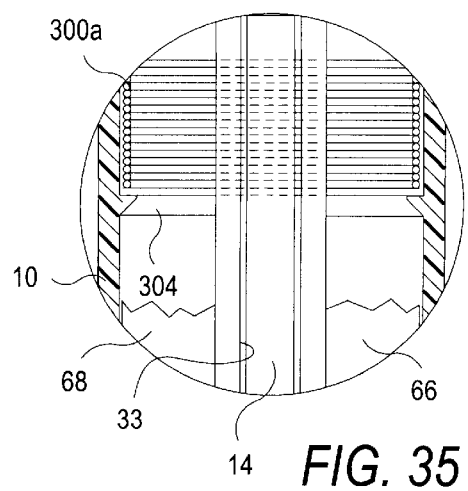
FIG. 35

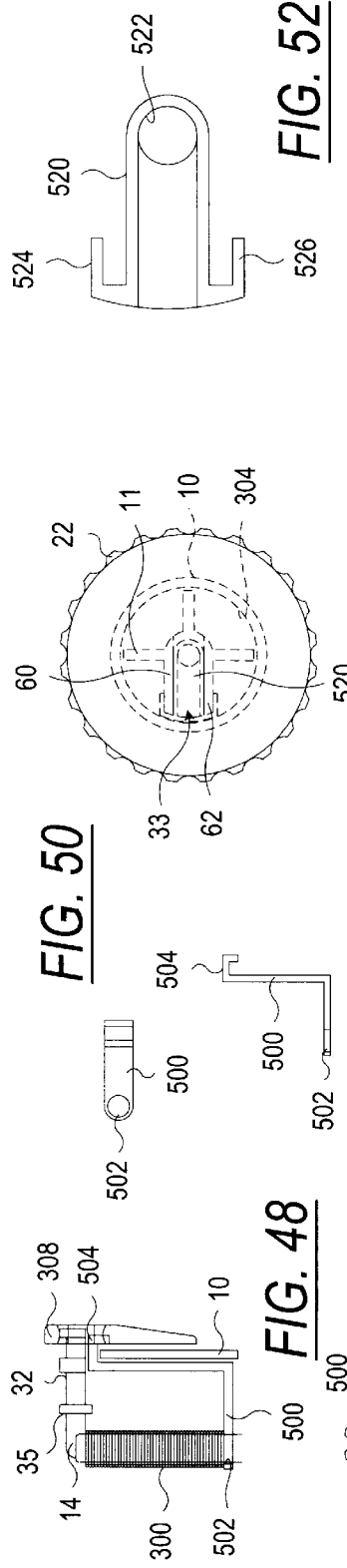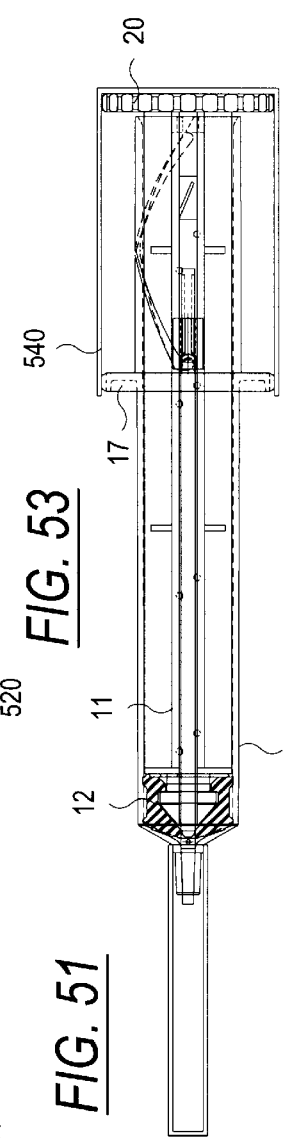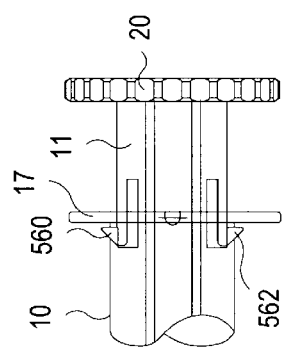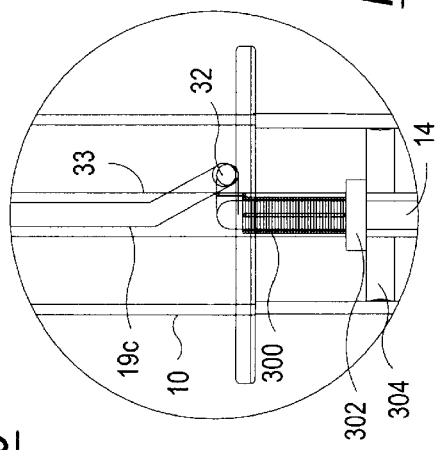

SAFETY SYRINGE

FIELD OF THE INVENTION

The present invention generally relates to syringes for use with hypodermic needles. In particular, the present invention relates to a needle-syringe a ssembly which withdraws the sharp point of the hypodermic needle following use so as to render it n on-reusable. An over-the-needle (OTN) catheter may also be used with the syringe assembly of the invention.

BACKGROUND OF THE INVENTION

A hypodermic needle has many applications in modern medicine. One application is to fit the hypodermic needle onto a syringe and to then insert the needle into a person's body for intra-muscular, subcutaneous, or intravenous injection of medications. Another application of the hypodermic needle is to coaxially mount a catheter over a hypodermic needle and to puncture a vein of a person's body with the needle. Following needle puncture, the over-the-needle (OTN) catheter is advanced into the vein, the needle is removed, and the catheter is connected to an intravenous line for fluid infusions into the vein.

A hypodermic needle entering into a patient's body is invariably contaminated by the patient's blood and body fluids. Following use of the needle, the needle presents a risk to physicians, nurses, and other health care personnel because the needle might transmit an infection or disease to such personnel if it were to accidentally puncture them. Thus, health care personnel are in constant danger of contracting infections and diseases, some of which may be deadly. Other potential victims of accidental needle punctures include sanitation workers who later dispose of garbage containing the hypodermic needle. The diseases which may be transmitted by a contaminated hypodermic needle include Immune Deficiency Virus, Hepatitis, Rabies, Kure, Encephalitis, and Arbor viruses. The outcome of contracting one of these diseases is often fatal because there are no known cures for any of these diseases. Often a needle puncture in a person's skin is so trivial that it remains unrecognized until the person becomes seriously ill.

Many existing OTN catheters suffer from penetration problems because of long length needles and unsecured needle supports. In addition, many existing OTN catheters still present the danger of causing needle pricks due to ineffective encasement of the needles following use.

Accordingly, there exists a need for a hypodermic needle assembly which overcomes the above-noted drawbacks associated with many existing assemblies.

The problem of suffering accidental needle punctures is well recognized. As a result, enormous inventive effort has been devoted to concealing the sharp needle point of hypodermic needles. One such effort is described in the present applicant's U.S. Pat. No. 5,338,311, issued Aug. 16, 1994.

SUMMARY OF THE INVENTION

One aspect of this invention comprises an improved needle-syringe assembly which provides a simple and reliable mechanism to retract the needle after it has been used.

Another aspect of the present invention comprises an improved needle-syringe assembly which facilitates fabrication, and reduces the cost, of the assembly.

Still another aspect of the present invention comprises an improved needle-syringe assembly which facilitates the operation of the assembly, particularly when it is desired to retract the needle prior to disposing of the needle-syringe assembly.

Another aspect of the present invention comprises an improved needle-syringe assembly which improves the acceptability of the assembly by providing an external appearance which is virtually the same as that of conventional hypodermic needle assemblies which do not provide for needle retraction.

A further aspect of the invention comprises an improved needle-syringe assembly that has the same length as conventional hypodermic needle assemblies which do not provide for needle retraction.

Another aspect of the invention comprises an improved needle-syringe assembly in which linear movements are employed for normal use and rotary movements for retracting and locking the needle in the syringe.

Yet another aspect of the invention comprises a needle-syringe assembly which provides for conventional operation for normal use, while needle retraction, once voluntarily activated, is automatic and complete.

Still another aspect of the invention comprises a needle-syringe assembly wherein the retracted position of the needle avoids puncture of the barrel and accidental sticking of medical staff.

Other aspects and advantages of the invention will become apparent upon reading the following detailed description and upon reference to the accompanying drawings.

In accordance with the present invention, a syringe assembly, operable in a normal mode and convertible to a retraction mode, comprises a safety syringe assembly which includes an elongated, generally cylindrical barrel having a hollow interior forming a hollow nozzle located at a distal end of said barrel and opening into the interior of said barrel, a plunger slidably mounted in said barrel and having a longitudinal cavity, a needle holder slidably mounted in said longitudinal cavity of said plunger for movement between an advanced position in which a needle on the distal end of said needle holder projects from a distal end of said nozzle and a retracted position in which said needle is retracted within said barrel, elastic biasing means mounted inside said barrel and coupled to said needle holder for urging said needle holder toward its retracted position, and a latch releasably engageable with said needle holder and movable between a closed position in which said needle holder is latched to hold said needle holder in its advanced position against the urging of said biasing means, and an open position in which said needle holder is unlatched to allow said biasing means to move said needle holder to its retracted position.

In accordance with another aspect of the invention there is further provided an over-the-needle catheter and means for releasably securing the catheter to the above syringe assembly.

Another aspect of the invention provides a method of sequential alignment and "single-stroke" in-barrel assembly of components which permits economical production of the device.

BRIEF DESCRIPTION OF THE DRAWINGS

In the drawings:

FIG. 7 is an elevation of a plunger element;

FIG. 8 is an end view of the plunger of FIG. 7;

FIG. 9 is a transverse sectional view of the plunger of FIG. 5;

FIGS. 10, 12, 14 and 16 are side elevations, with FIGS. 12 and 14 being in section, of various forms of barrel elements;

FIGS. 11, 13, 15 and 17 are end views of the barrel elements of FIGS. 10, 12, 14 and 16, respectively;

FIGS. 19–21 are partial elevations of a needle syringe assembly showing a latch in accordance with one embodiment of the invention;

FIGS. 22 and 23 are partial end views illustrating a latching mechanism in accordance with another embodiment of the invention;

FIGS. 24 and 25 are partial end views illustrating a latching mechanism in accordance with yet another embodiment of the invention;

FIG. 26 is a partial side elevation, partially in section illustrating a latching mechanism in accordance with another embodiment of the invention;

FIGS. 27, 28 and 29 illustrate a compression spring in accordance with one embodiment of the invention;

FIGS. 30 and 31 illustrate a compression spring in spring retraining element in accordance with one embodiment of the invention;

FIGS. 32a and 32b illustrate a compression spring in accordance with another embodiment of the invention;

FIG. 33 is a partial side sectional view illustrating assembly of the spring element and retainer of FIGS. 30 and 31 with a plunger and barrel of one embodiment of the invention;

FIG. 34 is a partial end view illustrating assembly of the spring element and retainer of FIGS. 30 and 31 with a plunger and barrel of one embodiment of the invention;

FIG. 35 is a partial sectional view similar to FIG. 33 showing a spring assembled with a barrel and a plunger in accordance with another embodiment of the invention;

FIG. 48 is a partial side elevation showing assembly of an alternate embodiment of a spring retaining member for engaging and retaining a distal end of a spring;

FIG. 49 is a reduced sized top plan view showing the spring retaining member of FIG. 48 in connection with a barrel and plunger;

FIGS. 50 and 51 are a plan view and side elevation of the spring support element of FIG. 48;

FIG. 52 is an enlarged plan view of another embodiment of a spring retaining element;

FIG. 53 is a partial top plan view of an assembled plunger and barrel incorporating the spring retaining element of FIG. 52;

FIG. 54 is a side elevation of an assembled needle and syringe assembly of the invention including additional packaging for a proximal end portion of the assembly in accordance with one embodiment;

FIG. 55 is an enlarged partial elevation showing a hybrid longitudinal and curved guide slot for a needle holder;

FIGS. 56 and 57 are views illustrating a barrel plunger lock in respective unlocked and locked positions;

DETAILED DESCRIPTION OF THE ILLUSTRATED EMBODIMENT

Figure 1:
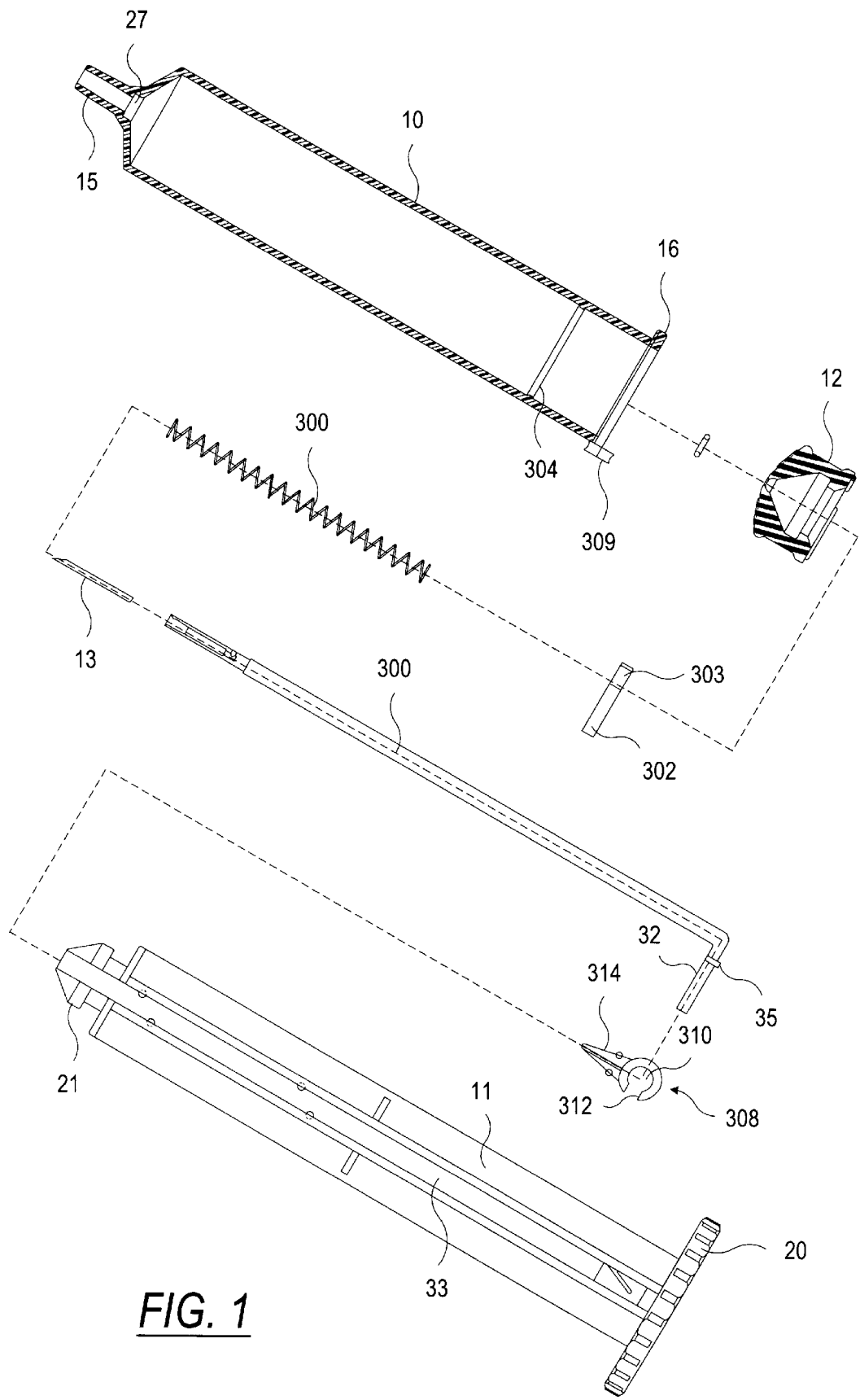
FIG. 1 is an exploded view illustrating parts of a needle and syringe assembly in accordance with one embodiment of the invention.

While the invention is susceptible to various modifications and alternative forms, specific embodiments thereof have been shown by way of example in the drawings and will herein be described in detail. It should be understood, however, that it is not intended to limit the invention to the particular forms disclosed, but on the contrary, the intention is to cover all modifications, equivalents, and alternatives falling within the spirit and scope of the invention as defined by the appended claims.

In order to satisfy the best mode requirement for this disclosure, several different modes of the invention, each with its own unique features and alternate embodiments, are described. Permutations and combinations of these features will, however, lead to further modes.

Turning now to the drawings, FIG. 1 illustrates a needle-syringe assembly including a barrel 10, a plunger 11, a hollow plunger cap 12, a hypodermic needle 13, and a needle holder 14. The barrel 10 is a hollow cylinder which terminates in a hollow tapered nozzle 15 at the distal end thereof, and has a slightly enlarged outer diameter 16 at a proximal end. The interior of the nozzle 15 communicates with the hollow interior of the tubular body portion of the barrel 10. As better seen in FIGS. 18 and 44–47, for example, an outwardly extending flange 17 near the proximal end of the barrel 10 facilitates gripping of the barrel with the user's fingers when it is desired to move the plunger 11 relative to the barrel 10 either linearly for normal use or rotatively for needle retraction (in some embodiments). The flange may be annular or oblong in the various embodiments.

The outer surface of the barrel 10 may contain graduations (not shown) indicating the volume level of fluid in the barrel. These graduations take into account the volume of the internal components such as the needle holder 14. A location 308 for a latch 308 (to be described later) is provided at a proximal end of the barrel 10.

The proximal end of the plunger 11 forms a knob 20 that can be grasped by a user to effect linear or rotary movement of the plunger 11 relative to the barrel 10. The periphery of the knob 20 is serrated to facilitate gripping of the knob for rotary movements of the plunger. The distal end of the plunger 11 forms a head 21 to accommodate the hollow rubber plunger cap 12. The outside diameter of the resilient cap 12 is reduced in the central portion so that the cap engages the inside wall of the barrel 10 only at the pliable margins of the ends of the cap. The diameter of the engaging end portions of the cap 12 is slightly larger than the inside diameter of the barrel 10 so that the cap presses firmly against the inside wall of the barrel to form an air-tight and liquid-tight seal at the cap/barrel interface. The inner margins of the cap 12 make a similar tight contact with the outer surface of the needle holder 14. The distal end 22 of the cap 12 is conical to conform to the conical distal end 23 of the inside surface of the barrel 10 when the plunger 11 is fully advanced within the barrel. The outer wall of the cap 12 may be thickened somewhat to prevent its collapse during the in barrel assembly process (described later).

The head 21 of the plunger 11 is configured to fit tightly within the hollow plunger cap 12. With the cap 12 locked onto the head 21 of the plunger, the flat proximal end 24 of the cap abuts the flat surface of a circular disc 25 at the base of the plunger head 21. Due to the air-tight and liquid-tight seal between the plunger cap 12 and the barrel 10, as well as the needle holder 14, advancing movement of the plunger 11 inside the barrel 10 creates pressure in the interior of the barrel between the plunger cap and the distal end of the barrel. Similarly, retracting movement of the plunger 11 creates a vacuum in that portion of the barrel interior.

Figure 5:
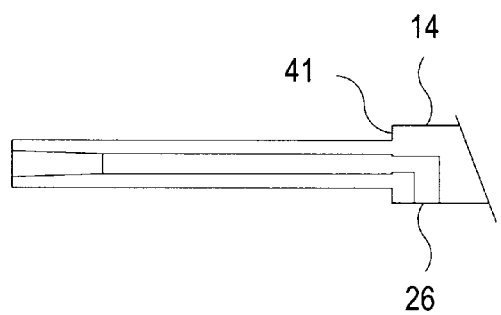
FIG. 5 is a partial sectional view of an end portion of a needle holder.
Figure 6:
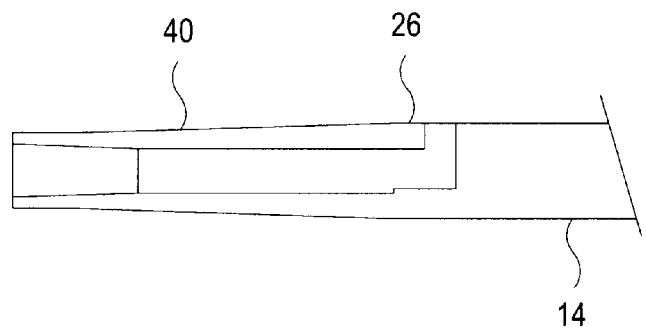
FIG. 6 is a partial sectional view of an alternate form of a needle holder end portion.

The hypodermic needle 13 is mounted on the distal end of the elongated needle holder 14, which is detachably interlocked to the barrel 10. Prior to use of the needle-syringe assembly, the needle 13 is covered by a protective cap 200 mounted on the nozzle 15 (see FIG. 44) which prevents needle pricks and preserves sterility prior to use. Both the needle 13 and the distal portion of the needle holder 14 are hollow, and the interior of the hollow needle 13 communicates with the interior of the hollow distal portion of the needle holder 14. The needle holder 14 further communicates with the interior of the barrel 10 through an aperture 26 which extends through the side wall of a hollow portion of the needle holder 14 at a distal end thereof (FIGS. 5 and 6). Prior to and during use of the needle-syringe assembly for injection of medicine or withdrawal of blood (hereafter referred to as "normal use"), the aperture 26 is positioned at the base of the barrel nozzle 15 (FIG. 18), sometimes within a small cylindrical cavity 27. The aperture 26 permits blood or medicine to enter or exit from the barrel 10 via the needle holder 14 and the needle 13. An O-ring 202 is located against a distal shoulder of the cavity 27 to promote sealing engagement with a distal end 203 of the needle holder 14 (see FIG. 18) when the distal end 203 is configured as shown in FIG. 5. A luer taper, described below, may be used as an alternate form of sealing.

During normal use of the needle-syringe assembly, the needle holder 14 is locked to the barrel 10, and the plunger 11 with its cap 12 are free to slide longitudinally back and forth along the needle holder within the barrel. In one embodiment, (see FIG. 2) the needle holder 14 includes an L-shaped rod 30 having a longitudinal body portion 31 extending to the aperture 26 and hollow from the aperture 26 to its distal end, and a lateral arm 32, for extending radially across the barrel 10, at a proximal end of the rod 30. The lateral arm 32 of the needle holder 14 may also include an enlarged diameter circumferential shoulder surface 35 for engagement with outermost surfaces of plunger ribs 60, 62 (described below) which form the channel 33, so as to position the needle holder 14 at the proper depth with respect to the channel 33.

Figure 18:
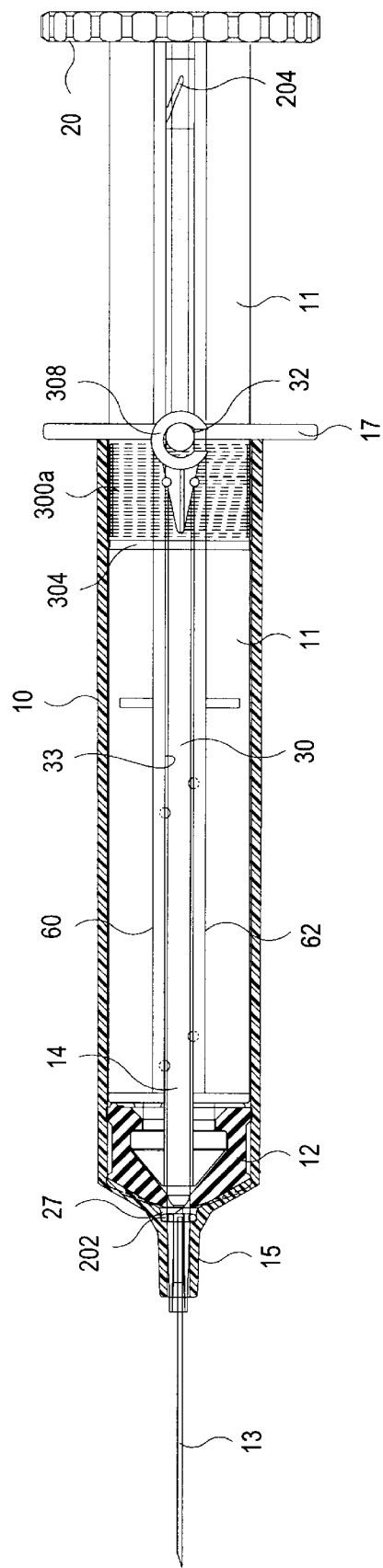
FIG. 18 is a plan view, partially in section of an assembled needle and syringe assembly having embodiment features according to one or more of the embodiments of the invention.
Figure 36:
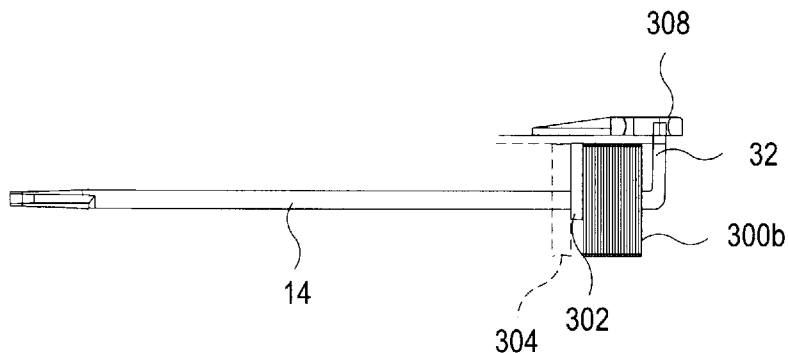
FIGS. 36 and 37 show operation of a needle holder with a biasing spring and latching elements in accordance with one embodiment of the invention.
Figure 37:
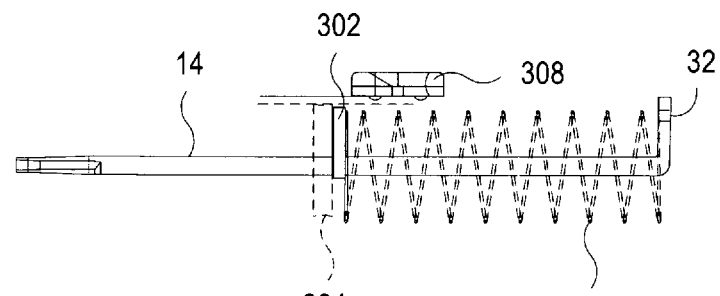
Figure 38:
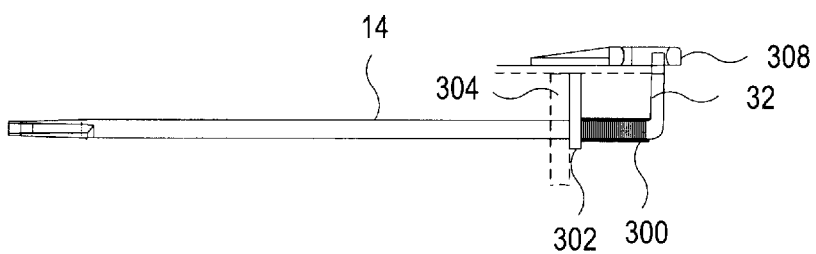
FIGS. 38 and 39 show operation of a needle holder element with a compression spring and element in accordance with another embodiment of the invention.
Figure 39:
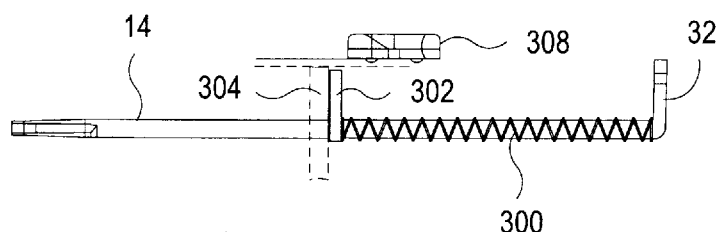

Referring also to FIGS. 7 and 18, to permit relative sliding movement between the plunger 11 and the needle holder 14 in the longitudinal direction, the needle holder is mounted in a longitudinal cavity or channel 33 formed as an integral part of the plunger 11. Multiple pairs of resilient retaining elements or detents 34 project toward each other from the opposed walls of the channel 33 to hold the needle holder 14 within the channel.

Referring to FIG. 9, the plunger 11 will be seen to have a plurality of ribs. A first pair of these ribs 60, 62 define the longitudinal channel 33 for receiving the needle holder 14 as described above. A single rib 64 projects diametrically oppositely of these ribs 60 and 62. A further pair of diametrically oppositely extending ribs 66 and 68 are formed in a plane at right angles to the ribs 60, 62 and 64. In accordance with one form of the invention, these latter ribs 66 and 68 may include recessed surfaces 70, 72 toward their proximal ends for purposes to be described later. These ribs 60–68, collectively extend transversely across the interior of the barrel 10 so as to help maintain the configuration of the barrel, for example, to counteract any weakness caused by the slot 19. This also helps to ensure the engagement of the lateral arm 32 with the slot 19.

In some embodiments, the opposed walls or ribs 60, 62 of the channel 33 extend all the way to the inside wall of the barrel 10 (see FIG. 9), thereby constraining the lateral arm 32 of the needle holder against any angular or rotational displacement relative to the plunger 11. That is, the plunger 11 and the needle holder 14 can rotate only in unison with each other, although they move independently of each other in the longitudinal direction. At the proximal end of the channel 33, a locking detent 75 locks the lateral arm 32 and plunger together to prevent relative longitudinal movement after retraction of the needle holder 14 is complete.

Figure 4:
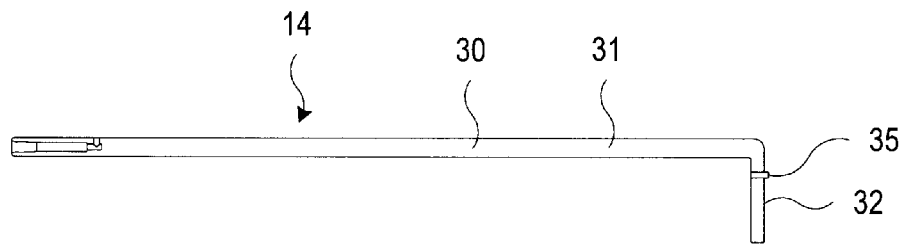
FIG. 4 is an elevation of another embodiment of a needle holder.

In the embodiment shown in FIGS. 4 and 6, to lock the needle holder 14 to the barrel 10, the outer surface of the distal end portion of the needle holder 14 is molded to form a tapered surface 40 which mates with a complementary tapered surface 15a (e.g., FIGS. 10 and 16) on the inside wall of the barrel nozzle 15. These tapered surfaces are conventionally known as locking luer tapers, and the angle of the taper (typically 6% of the diameter) is conventionally known as a locking taper angle. In one embodiment, the taper has a length between about 0.185 and about 0.250 inch with a diameter of 0.094 inch at one end and a diameter of 0.082 inch at the other end.

The locking tapered surfaces are engaged during assembly of the needlesyringe assembly, when the plunger 11 and needle holder 14 are inserted into the barrel 10 through the open proximal end of the barrel. The resultant locking luer taper can be released by the application of simultaneous axial and rotational forces.

In another embodiment (FIGS. 3 and 5) the distal end of the needle holder is straight (not tapered) and stepped down to provide a shoulder 41 for sealing engagement with the O-ring 202 provided in the cavity 27 (FIG. 18). The corresponding interim surface of the nozzle 15 is also non-tapered and stepped to form the cavity 27. The outside surface of the nozzle 15 may have a male luer taper to lockably engage a female luer of an over-the needle catheter, as described below with reference to FIGS. 60 and 61.

In some embodiments (see e.g. FIGS. 14 and 16), the proximal end of the needle holder 14 is locked to a proximal extension of the barrel 10, via the lateral arm 32. This arm 32 extends radially beyond the plunger and fits into a slot 19 in the sleeve 18. The arm 32 can be locked to the barrel 10 at the margin or distal end of the slot 19 and, when so locked, permits only reciprocal linear movement of the plunger 11, to create vacuum to withdraw medication or blood and pressure to deliver medication to the patient via the hypodermic needle. When the above-described luer taper engagement between the needle holder and barrel is used, the slot 19 is helical (see FIGS. 16 and 43–44) to permit the rotation needed to release the luer taper locking. However, when the arm 32 is locked at either end of the slot 19, the plunger 11 cannot be rotated within the barrel 10. When the arm 32 is also locked in a plunger detent 75 (FIG. 7), following use, the entire assembly is interlocked and inoperative.

In the advanced position, as illustrated for example in FIGS. 2, 18 and 44–45, the needle holder holds the needle completely advanced or projecting from the body of the barrel 10 for normal use. Referring again to FIG. 1, in accordance with a feature of the invention, a retracting means, such as an elastic or resilient biasing means, here illustrated as a compression spring 300 is mounted inside the barrel 10 and operatively contacts the needle holder 14 for urging the needle holder toward its retracted position, that is a position in which the needle 13 is retracted completely within the barrel 10 (see e.g., FIGS. 46–47). In the embodiment illustrated in FIGS. 1 and 2, the elastic biasing means takes the form of an elongate compression spring 300 of relatively small diameter which fits about the outer circumference of the needle holder 14. This spring 300 is of such a diameter that it also interfits within the elongated channel or cavity 33 of the plunger 20. However, the elastic biasing means or spring may take a number of other forms, some of which will be described hereinbelow, without departing from the invention.

Figure 2:
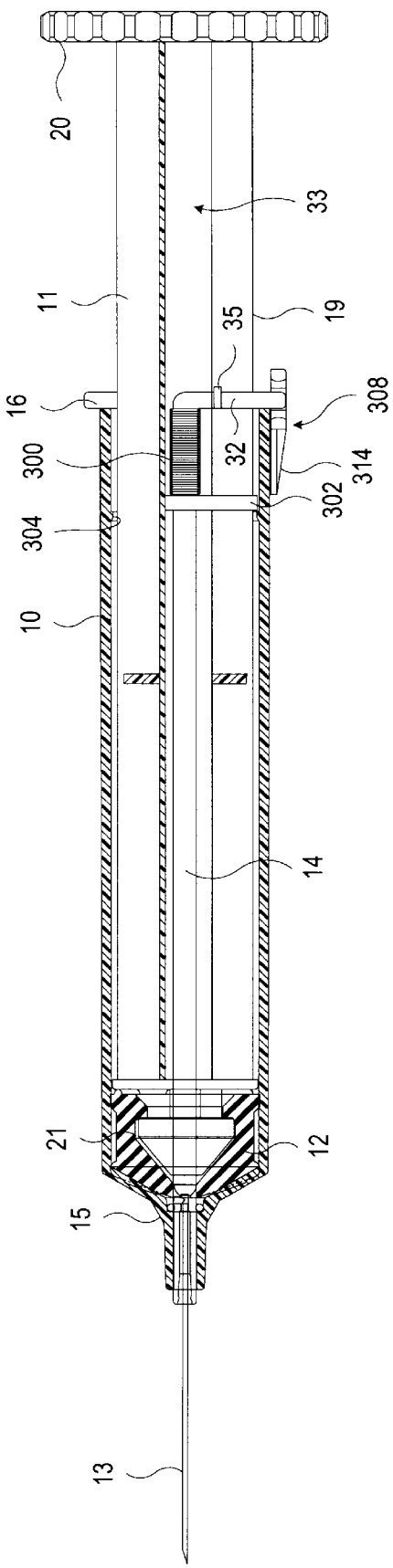
FIG. 2 is an assembled view of the needle-syringe assembly of FIG. 1.
Figure 3:
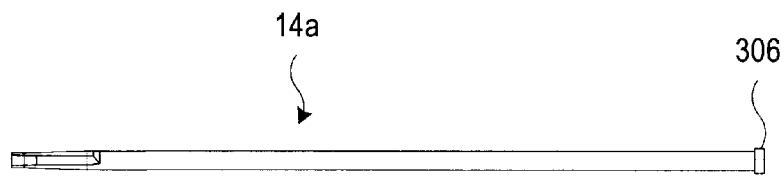
FIG. 3 is an elevation of a needle holder.

In the embodiment illustrated in FIGS. 1 and 2, a first spring retaining means or member 302 takes the form of a relatively short piece of material having a through aperture 303 at one end thereof for fitting about the circumference of the needle holder 14 while allowing sliding movement therebetween. The member 302 is arranged to engage an inwardly extending annular rim 304 which is formed in the interior surface of the barrel 10 at a proximal end portion thereof. This retaining member 302 thus engages and retains in place a distal end of the spring 300, so as to exert a force against the opposite or proximal end of the needle holder 14. In the embodiment shown in FIGS. 1 and 2, the needle holder 14 is of the type which includes a laterally extending arm 32 at its distal portion. However, as shown in FIG. 3, the needle holder 14a may instead include an enlarged diameter annular rim or other enlarged profile portion 306 at its proximal end for abutting and engaging the proximal end of the spring 300. With reference to FIG. 2 (and also FIGS. 45–46), it will be seen that with the needle in its advanced position, the spring 300, which is a compression spring, is in a compressed condition, thereby applying an urging or biasing force against the needle holder 32.

In order to control the position of the needle holder 14 relative to the barrel 10 for presenting the needle either fully advanced or fully retracted with respect to the barrel, there is additionally provided a latching means or mechanism 308.

In the embodiment shown in FIGS. 1 and 2, the latching mechanism 308 takes one form. However, other equivalent forms may be used without departing from the invention, some of which are further described hereinbelow. In the embodiment shown in FIGS. 1 and 2, the latching element comprises a needle holder locking element 308, having a central aperture 310 which interfits about a free end portion of the radially projecting arm 32 of the needle holder 14 which projects outwardly of the slot 19 in the barrel 10, as shown in FIG. 2. The latching element 308 includes a small opening 312 in its circumference with sufficient width to allow the lateral arm 32 to pass therethrough when the two are in alignment. As also shown in FIG. 2, the latching element 308 when in its latched position contains the needle holder in its advanced position and the spring 300 full compressed. However, the latching element 308 is rotatably mounted to the needle holder locking site 309 at a proximal external side surface of the barrel 10, to permit rotation, by engagement with a lateral arm portion 314 thereof, in a direction for aligning the opening 312 with the free end of the lateral arm 32. When this occurs, the biasing force of the spring 300 will cause the needle holder 14 to rapidly withdraw to its retracted position and thereby fully retract the needle 13 within the barrel 10. As mentioned above, the detent or retaining element 75 at the proximal end of the plunger channel or cavity 33 thereupon non-releasably engages the lateral arm of the needle holder to retain it in the retracted position.

When the barrel takes the form shown in FIGS. 12, 18 and 44–47, the needle holder 14 can also be released from the latching element 308 by effecting relative rotation of the barrel and the plunger, to cause the lateral arm to rotate laterally out of engagement with the latching element 308 through its opening 312. This relative rotation can be effected by engaging the finger flange 17 and knob 20. Moreover, this rotation can be effected with one hand, for one-handed retraction.

The structure and operation of the latching element 308 of FIGS. 1 and 2 is also shown in FIGS. 10, 12, 14, 18–21, 37–40 and 44–47, in connection with elastic biasing or retracting means, such as springs, of various forms, including as well as in addition to the form of the spring 300 illustrated in FIGS. 1 and 2. As noted above, the latch mechanism 308 includes a manually engageable lever portion 314 for effecting the desired rotation for release of the lateral arm 32 of the needle holder 14 therefrom.

Figure 4A:
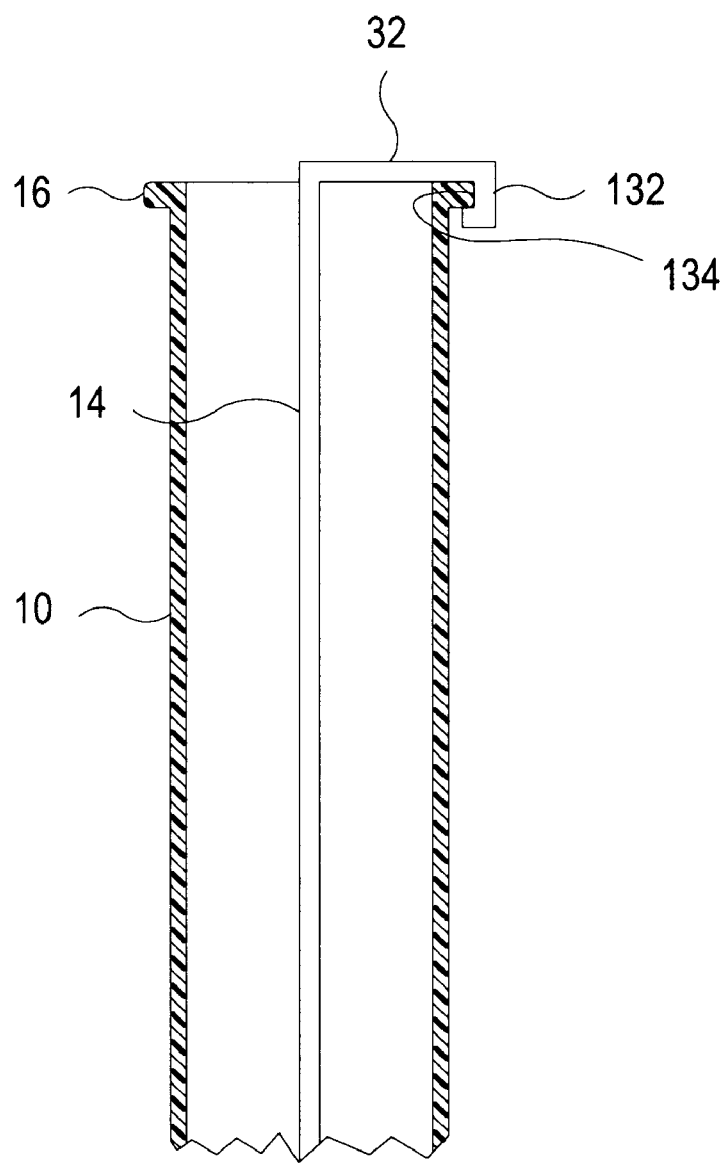
FIG. 4a is a partial view of modified portion of the needle holder of FIG. 4.

Releaseable latching of the needle holder relative of the barrel can be effected in other ways without departing from the invention. For example, as shown in FIG. 4a, the lateral arm 32 may have an additional 90° bend 132 and an undercut 134 which may releaseably lockingly engage or latch with the rim 16 formed at the proximal end of the barrel 10, as indicated in FIG. 4a, when the barrel is of the form in FIGS. 12, 18 and 44–47. Alternately (not shown), the engagement could be with the wall of the barrel at a distal end of the guide channel or slot 19.

When the user desires to retract the hypodermic needle 13 within the barrelplunger assembly, the mechanical latch is manually actuated to unlock the arm 32 and thereby permit withdrawal of the needle holder (and rotation of the plunger 11 in the case where the channel 19 is a helical) relative to the barrel 10. This motion retracts and locks the needle-needle holder assembly within the barrel-plunger assembly, as indicated above. For the needle and needle holder to be moved to the retracted position, the plunger 11 can be in any desired position, e.g., to permit blood or medication to be retained in the syringe, as shown for example in FIGS. 46 and 47).

That is, when the latch is opened to retract the needle holder, the plunger can be in any desired longitudinal position. For example, the plunger can be fully advanced, fully retracted, or at any intermediate position. This is advantageous because it might be desired to retract the needle after only a portion of a dose of medication has been injected into the patient, or it might be desired to retain all or a portion of a blood sample withdrawn from a patient within the syringe. To prevent the leakage of any fluid contained within the syringe at the time the needle is retracted, a latex seal (not shown) may be provided at the end of the nozzle 15. Also, the plunger cap 12 may be provided with a slit valve that engages the needle and prevents leakage.

During normal use of the needle-syringe assembly, the barrel 10 and the needle holder 14 are held stationary, and the plunger 11 is free to move relative to both the barrel 10 and the needle holder 14. Advancing movement of the plunger 11 is limited by contact of the plunger cap 12 with the end wall of the barrel 10, as shown in FIG. 1. The needle holder 14 is releasably locked to the barrel 10 by the locking engagement of the lateral arm 32 to the wall of the barrel by a latch such as the latch 308. Also, when used, the locking luer taper releasably locks the needle holder 14 to the barrel 10. The plunger 11 is also free to move longitudinally relative to the needle holder 14, as illustrated in FIGS. 45–48, because the needle holder is not locked to the plunger in that direction. The locking of the lateral arm 32 by the latch mechanism 300 at the barrel wall, prevents rotation of the plunger. As long as the lateral arm 32 of the needle holder is locked to the barrel wall, the needle-syringe assembly is in its normal operating mode.

Following normal use of the needle-syringe assembly, the needle 13 can be retracted into the plunger 11 and the barrel 10. This requires axial movement of the needle holder 14 within the barrel 10 toward the proximal end thereof, which in turn requires that the needle holder 14 be unlocked for movement, under the influence of the biasing or retracting means such as spring 300, along the slot 19. Thus, to initiate retraction of the needle holder 14, the arm 32 is unlocked by releasing the latching mechanism 308.

Figure 46:
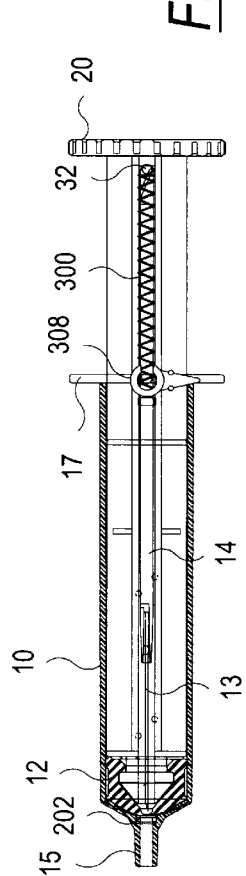

When the slot 19 is a helical, rotation of the needle holder 14 relative to the barrel releases the locking luer taper at the distal end of the barrel nozzle 15 due to the resulting compound rotational and longitudinal forces applied to the tapered surfaces. The arm 32 traverses the entire length of the slot 19 (whether linear or helical), thereby retracting the entire needle holder 14 through a corresponding axial distance within the plunger 11 (see FIG. 46). Of course, the needle 13 is retracted along with the needle holder 14, and thus the needle is retracted completely within the barrel nozzle 15, as illustrated in FIG. 46.

The helical slot 19 (when used with the luer taper) is formed in a proximal end portion of the barrel 10. The helical slot may have a constant rate of curvature along its length. Alternatively, a helical channel can be molded as a part of the inside wall of a proximal end portion of the barrel that has a slight wall thickness (not shown). The syringe structure might employ a modified form of latch instead of latch 308, for example as shown in FIGS. 24–25. Yet another alternative is a slot 19b as shown in FIG. 55 which has an angled or curved distal portion of sufficient extent to cause rotation of the needle holder sufficiently to release the locking luer taper, and is thereafter straight. The illustrative syringe need not be any longer than a conventional syringe because conventional syringes are made longer than required to provide more than the desired fluid volume, so as to avoid inadvertent withdrawal of the plunger and the resultant spillage of the syringe contents. The extra plunger barrel length to accommodate the user's fingers in the space between the plunger knob and the finger flanges contributes to excess length in conventional syringes. In the present invention, the extension of the barrel length in this area can be used for slot 19 of the needle-retracting mechanism.

Referring now to the remaining FIGS. 10–47 of the drawings, a number of alternative structures and arrangements of the syringe assembly are illustrated and will be described hereinbelow. These alternative structures or embodiments include, among other things, alternative embodiments of barrels, retracting means or an elastic biasing means for retracting the needle holder 14, including primarily alternative forms of spring to the spring 300 shown in FIGS. 1 and 2. These alternate embodiments also include various embodiments of a latching mechanism or latching means for releasably holding the needle holder in its advanced position with the needle extended from the barrel 10 of the syringe (as shown for example in FIG. 2) against the biasing force of the retracting or elastic means or resilient biasing means.

As shown in FIGS. 10–17, the barrel may be provided in various lengths, with the latching means or mechanism 308 in FIGS. 12–15 being essentially the same as illustrated and described above with reference to FIGS. 1 and 2. It will be noted that a linear channel 19 is illustrated in FIGS. 10 and 14–15. The barrel of FIGS. 12–13 is too short to include a channel 19, whereby the needle holder 13 is retracted within the channel or cavity 33 of the plunger, but does not require any corresponding slot in the barrel 10 to permit passage thereof during retraction. This embodiment could also be used with the locking taper described above. In FIGS. 10–11 an additional outwardly extending protective rib member 210 is illustrated for overlying the linear channel 19 and permitting access to the laterally extending arm 32 of the needle holder 14 to permit engagement thereof with the barrel while concealing the spring or other biasing or retracting means, following release thereof by the latching mechanism 308 and retraction of the needle. FIG. 16 shows the helical slot configuration 19 and the associated latching mechanism which is more fully described hereinbelow.

FIGS. 18 and 35 show a second version of the spring 300, designated by reference numeral 300a. The spring 300a is of a larger inside diameter so as to interfit about an outermost surface of the respective ribs 60, 62, 64, 66 and 68 which comprise the plunger 11. The gripping flange 17 is also illustrated in this figure.

FIGS. 22–23 and 24–25 illustrate two further forms of latching mechanism 308, here designated by reference numerals 308a and 308b. The latching mechanism 308a may operate with the form of the needle holder 14a shown in FIG. 3, that is, without the lateral arm 32 but with an enlarged diameter end portion 306 to engage the coil spring 300. The latch mechanism 308a comprises a spring-clip-like member 320 which is collapsible as shown in FIG. 23 by manipulation of an outwardly extending ear or tab 322. When in its extended condition the spring latch 320 has an outwardly extending arm 324 which overlies and engages an end portion of the needle holder 14a. When retracted, the needle holder 14a is free to retract under the influence of the spring 300 or other retracting or biasing means.

A similar spring-clip-like device 330 is illustrated in FIGS. 24–25. This element 330 also has an outwardly extending manually engageable release tab or button 332 which causes the spring member 330 to collapse as shown in FIG. 25, so as to release the lateral arm 32 of the needle holder 14. It will be noted that one leg or portion 334 of the spring clip 330 overlies a projecting free end portion of the lateral arm 32 in FIG. 24 but is released from such engagement upon activation of the release lever 332 in FIG. 25. The latching mechanisms 308a and 308b are shown mounted on an outwardly extending finger flange 17, which may comprise an integral portion of the barrel 10, as mentioned above. The respective spring members 320 and 330 may be mounted in molded recesses or compartments formed within the flanges 17 and which may be provided with integrally attached protective covers 326, 336.

Alternatively, a hinged locking tab 59 (FIG. 26) connected by a living hinge 61 to the barrel 10, may be provided. The tab 59 has a through aperture 63 for engaging the lateral arm 32 at the distal end of the slot 19. One or more detents 65 on the outer wall of the barrel 10 may hold the tab in place when engaged with the lateral arm 32 of the needle holder 14. Also, the lateral arm 32 may have a snapping detent to engage the barrel proximal end or rim.

FIGS. 19–21 illustrate yet another form of the spring 300, designated by reference numeral 300b, together with further details of the latching mechanism 308.

FIG. 26 shows the spring 300b with the hinged latching mechanism described above.

The spring 300b is sized with an inner diameter to fit about an outer surface of the plunger 11, with the plunger 11 being designed in FIGS. 19–21 with a recessed area 338 in the ribs in which to mount and receive the spring 300a. This recess in the ribs of the plunger 11 will provide a stop surface for engaging the distal end surface of the spring 300a. In FIGS. 19–21, both the barrel 10 and plunger 11 have smaller outer diameters than in the preceding FIGS.

Alternatively, as shown in FIG. 26, the plunger 11 has a smaller outer diameter (shorter ribs 60–68) and the barrel has the same outer diameter as in FIGS. 1 and 2. Also, in FIG. 26, the distal surface of spring 300b may be engaged in position by an annular retaining disc 340 which is engaged with the annular inwardly projecting shoulder 304 of the barrel 10, described above. The annular disc 340 has a through central opening 342 of sufficient diameter to allow the plunger to freely pass therethrough while engaging and providing a stop surface for the distal end of the spring 300b.

FIGS. 27–30 and 32 illustrate various alternative forms of the spring designated 300c, which may include a laterally extending distal end portion 350 for engagement with the distal end stop member 302 or which may engage the rim 304 of the barrel, eliminating the stop 302. A hook-like proximal end extension 352 is also provided for engagement about the lateral arm 32 of the needle holder 14. FIGS. 30 and 31 show the spring 300 and stop 302 and FIG. 32 shows spring 300b for purposes of comparison. FIGS. 33 and 34 also show other views of the spring 300, stop 302, rim 304, and the rod 30 and lateral arm 32 of the needle holder 14, while FIG. 35 shows an embodiment with the larger diameter spring 300a and rim 304, again, for purposes of comparison.

FIGS. 36–39 illustrate the action of the latching mechanism 308 of FIGS. 1 and 2 in connection with the needle holder 14 and its lateral extension or arm 32 using both a small diameter spring 300 and a relatively larger diameter spring such as the springs 300a or 300b described above.

Figure 43:
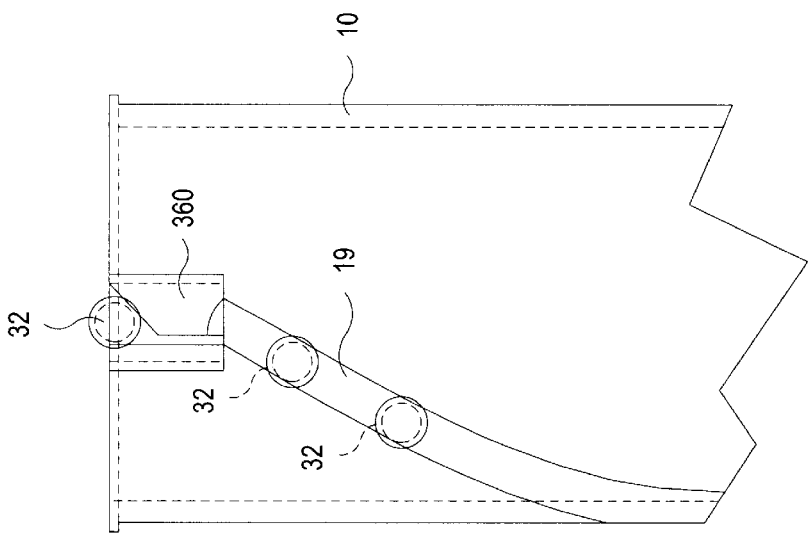
FIG. 43 is an enlarged partial elevation illustrating the detent locking of a needle holder in a proximal end of a barrel having an assembly slot in accordance with one embodiment of the invention.
Figure 42:
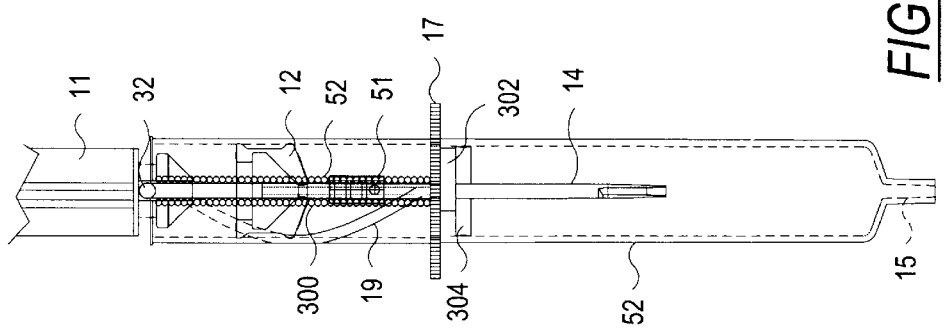
FIGS. 40 and 42 are side elevations, and FIG. 41 an end view, illustrating one method or sequence of "in-barrel" assembly of a needle-syringe assembly of the invention.
Figure 41:
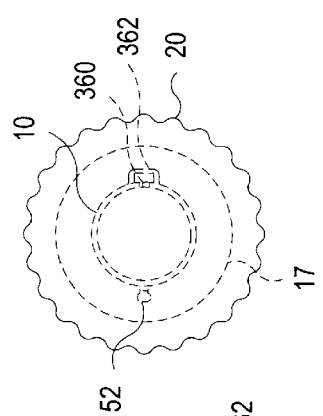
Figure 40:
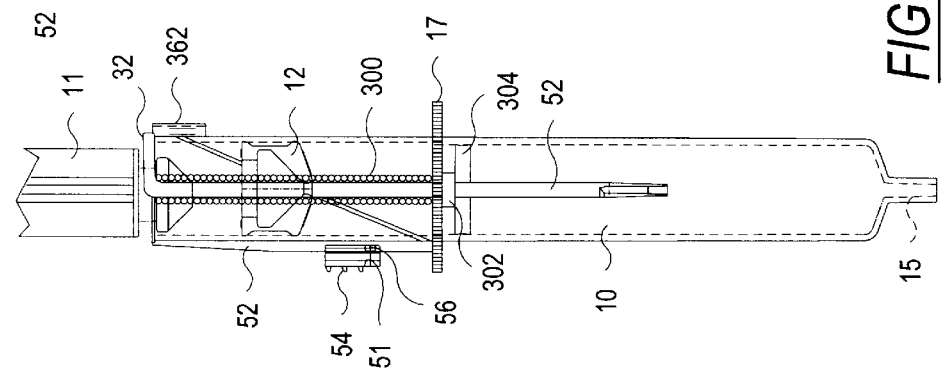

FIGS. 40–43 illustrate an embodiment utilizing a helical channel 19 in the barrel 10. FIGS. 40–42 also show a simple method of assembly of the invention wherein the cap 12 and needle holder are axially inserted in the barrel 10, followed by the plunger 11, with the channel 33 aligned to slidably receive the needle holder 14. While FIGS. 40–41 show the helical track 19 and latching mechanism 50 or rib 52, the same method of assembly applies to the other embodiments shown and described herein. FIG. 43 also shows a proximal end detent 320 for retaining the lateral arm 32, once retracted, at the proximal end of the helical track 19.

Figure 44:
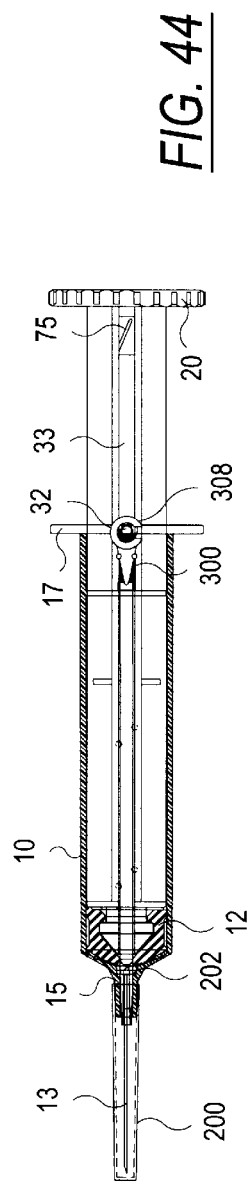
FIGS. 44–47 illustrate various stages or phases of operation of a needle syringe assembly in accordance with one embodiment of the invention.
Figure 45:
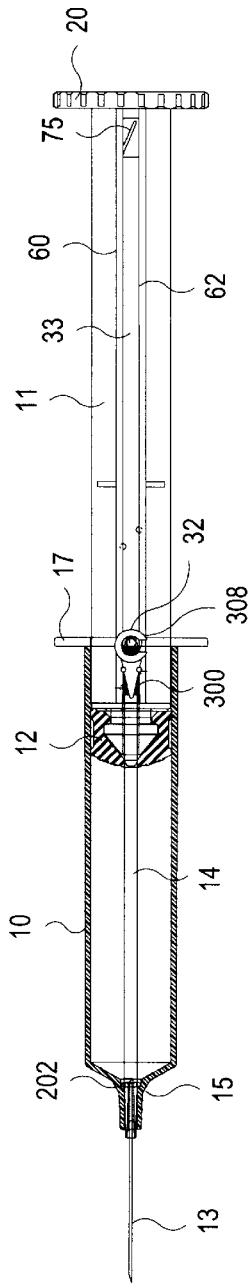

FIGS. 44–47 illustrate various positions of the assembly of FIGS. 1 and 2. FIG. 44 illustrates the assembled syringe and needle assembly with the cap 200 in place as it might be provided for use. FIG. 45 illustrates the assembly with the cap 200 removed and the plunger 11 withdrawn, as would be done, for example, to introduce a medication into the syringe or to withdraw blood from a patient.

Figure 47:
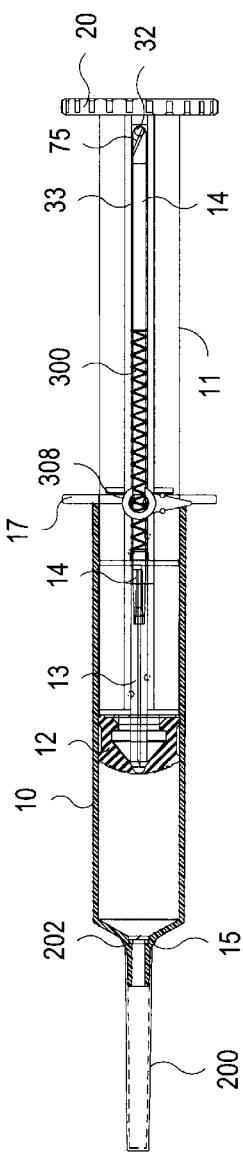

FIG. 46 illustrates the assembly fully advanced, with the needle holder 14 and needle retracted, following release of the spring 300 by the latching mechanism 308. FIG. 47 illustrates the needle holder 14 and needle 13 retracted relative to the plunger 11, but with the plunger partially withdrawn from the barrel 10, as would be the case with some medication or other fluid remaining in the syringe, following use thereof, and with the cap 200 replaced to prevent leakage of the remaining fluid within the barrel 10.

The alternative latch mechanism of FIGS. 16–17 and 40–42 is used with the helical track 19 and includes a longitudinally grooved tab 51 mounted for sliding movement upon a short longitudinal track 52 on the outer wall of the barrel 10. The groove (not shown) of the tab 51 is shaped to match the outer surface of the track 52 so that the tab 51 slides back and forth on the track 52. The outer surface 54 of the tab 51 is serrated to facilitate movement thereof with the user's finger or thumb.

The locking tab 51 also includes a small recess 56 formed within the groove 53. This recess 56 is sized and located to engage a terminal end part of the lateral arm 32 of the needle holder 14, when the lateral arm 32 is at a distal end portion of the helical slot 19 with the needle 13 in a fully extended position. This prevents the tab from sliding in the proximal direction along the track 52. This engagement can be overcome by a deliberate manually applied force to retract the tab 51 when it is desired to retract the needle.

The latch 50 can be opened or closed by linear movement of the locking tab 51 along the track 52. During normal use, the needle holder arm 32 is positioned at the distal end of the helical slot 19, which is immediately adjacent the flange 17, and the locking tab 51 is advanced on the track 52 to retain the arm 32 at the distal end of the slot 19. This locks the needle holder 14 in the normal operative mode in which only linear reciprocal movement of the plunger 11 is permitted. Because the locking tab 51 retains the arm 32, the needle holder 14 cannot rotate and thus cannot travel along the helical slot 19 for retraction of the hypodermic needle 13.

When it is desired to retract the needle, the tab 50 is retracted along the track 52 toward the proximal end of the syringe, thereby permitting rotation of the plunger 11 and retraction of the needle holder 14 by movement of the arm 32 along the helical slot 19, driven by the spring 300. A proximal end of the helical slot 19 may include a locking feature 320 to lock the end of the arm 32 in place when the needle holder has been fully retracted. Also illustrated in FIG. 43 are several approximate positions of the lateral arm 32 of the needle holder 14 as it is rotated relative to a proximal end portion of the helical slot 19. The needle holder 14 ascending proximally on the helical 19 slot passes into the locking feature 320, snapping into the locked position with a click.

Figure 58:
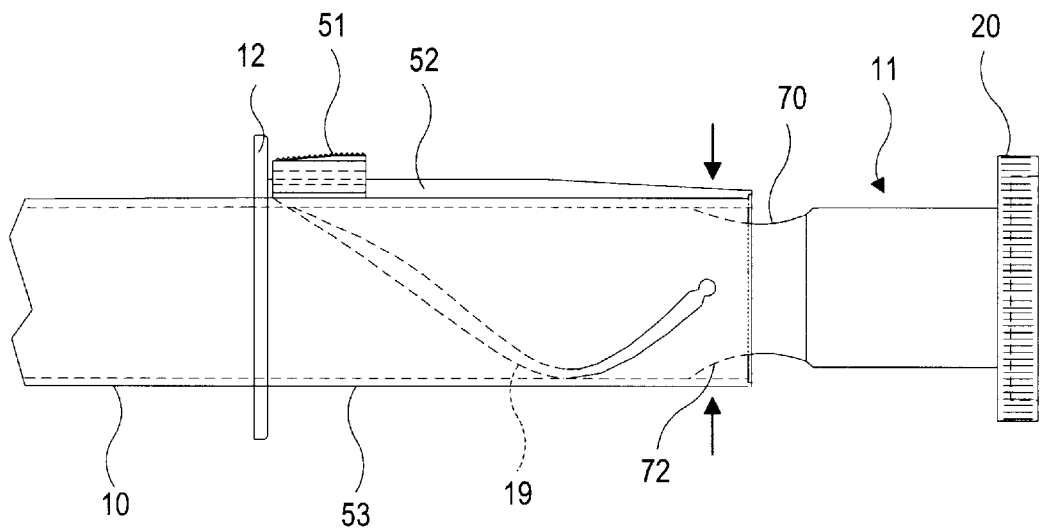
FIGS. 58 and 59 are a partial elevation and a partial end view, partially in section, illustrating a feature in accordance with another embodiment of the invention.
Figure 59:
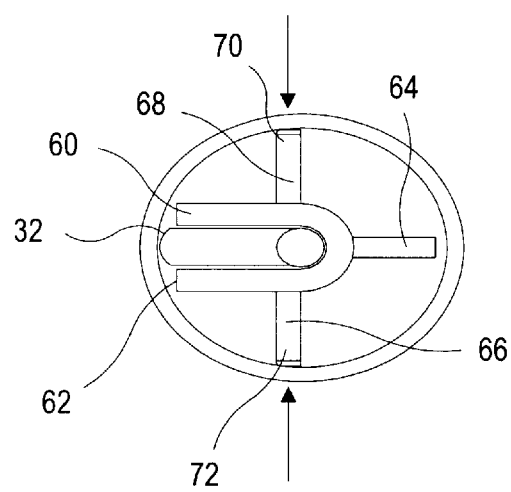

Referring to FIGS. 58–59, with the plunger 11 partially withdrawn with respect to the barrel 10, the recessed surfaces 70 and 72 of the ribs 66 and 68 provide a relief space for a proximal end part of the barrel 10 when opposed walls of the open end of the barrel 10 are pressed toward each other, for example by applying pressure between a thumb and a finger. As best viewed in FIG. 51, this action momentarily distorts the proximal open end of the barrel 10 to a somewhat elliptical shape so as to permit the initial insertion of the lateral arm portion 32 of the needle holder 14 past the proximal open end of the barrel 10 and into the helical slot 19. When the pressure on the barrel 10 is released, it resumes its generally circular cross-sectional shape for retaining the lateral arm 32 in engagement with the helical slot 19.

To operate the needle-syringe assembly, the protective cap 200 (FIG. 44) is removed from the needle 13, and the required amount of medication is aspirated into the barrel 10 (FIG. 45). Next, the injection site on the body of a patient is determined and the skin is cleaned with an antiseptic solution. Following percutaneous entry of the needle into the patient, location of the needle tip in the vein is confirmed by aspirating a small amount of blood into the transparent barrel 10. The plunger 11 is then advanced to force the medication from the barrel 10 into the vein. After the medication is administered, the needle 13 is withdrawn from the patient, the latch mechanism 308 is released and the spring 300 or other retracting means retracts the needle holder 14 and the needle 13 (FIG. 46 or FIG. 47) and locks the needle holder in the plunger detent 75. With the needle 13 completely retracted inside the barrel 10, interlocked and non-reusable, the needle-syringe assembly can be safely discarded in its entirety.

It can be seen from the foregoing description that the needle-syringe assembly performs all the conventional functions of injection syringes and yet, upon completion of injection, the hypodermic needle 13 is concealed within the barrel 10. The needle-syringe assembly can receive and disperse medications any number of times for a given patient by reciprocal longitudinal movement of the plunger 11 within the barrel 10. However, once the latch is released it cannot be reused.

The needle-syringe assembly of this invention is easy to manufacture, costeffective, and easy to use in the field. The parts can all be made by conventional plastic molding and using readily available metal needle stock. The plastic parts can be made by injection molding medical grade polymers such as polypropylene. The plunger seal or cap can be molded from natural or synthetic elastomeric polymers. The helical channel on the inside wall of the barrel (if used) can be molded with slides or rotating cores which are removed by rotating them while withdrawing them from the molded part.

Because the needle holder 14 is retracted directly into the plunger 11 itself, the plunger 11 need not be fully extended for needle retraction to occur. Thus, when discarded following use, the needle-syringe assembly contributes minimally to the bulk of refuse. Since retraction of the needle 13 is effected by the spring or other elastic biasing means, upon releasing the latch, the hand of a user does not come into the vicinity of the needle point, thereby minimizing the possibility of a needle prick during retraction. Moreover, the assembly employs substantially the same number of components as conventional syringes, and does not require additional guards, sheaths, sleeves, etc. to conceal the needle following use.

Referring to FIGS. 48–57, some alternative forms of various parts and components heretofore described are illustrated. FIGS. 48–51 illustrate an alternate form of a retaining member 500 for retaining a distal end of the spring 300 in place. The retaining member 500 is a generally L-shaped bracket, having a projecting lateral arm portion 501 with a through aperture 502 for permitting the needle holder 14 to slide therethrough while retaining the spring 300 in place about the needle holder 14. The lateral arm 501 of the retaining member 500 is of a width to interfit within the channel or cavity 33 of the plunger 11. An upper end of the retaining member 500 includes a hook-shaped lateral projection 504 which may hook through and over an outer wall of the barrel 10, for example, at a bottom portion of the slot 19, just below the point at which the lateral arm 32 extends therethrough and engages the latching member 308. The L-shaped bracket 500 could also be molded as an external part of the barrel, and folded into place inside of the barrel during assembly.

FIGS. 52 and 53 show yet another embodiment of a spring retaining element 520 for retaining the distal end of the spring 300. This element has a through aperture 522 for permitting the needle holder 14 to pass through, while retaining the spring 300 in place. The element 520 is of a width to interfit within the channel or cavity 33 of the plunger 11. An end portion of the retaining member 520 has outwardly projecting arms 524 and 526 for embracing the respective ribs 60 and 62 which define the channel 33. An outer end surface of the retaining member 520 may rest upon the annular rim 304 of the barrel 10.

FIG. 54 illustrates an assembled needle-syringe assembly in accordance with the invention which has been further provided with a protective cylindrical sheath, covering or packaging 540 which extends between the large knob 20 at the end of the plunger and the finger flange 17, which in the embodiment of FIG. 54 is generally annular in shape. This protective sheath or covering 540 protects and prevents access to the latch and retracting mechanism prior to use. When ready for use, the protective sheath or packaging 540 may be removed from the needle-syringe assembly.

FIG. 55 illustrates an alternate form of channel 19c, in which a distal end portion is angled curved to facilitate initial release of a luer locking taper, where one is used between the needle holder 14a and nozzle 15. Thereafter, the channel 19c is straight and axial to permit a linear longitudinal retraction of the needle holder 32 under the influence of the spring 300.

FIGS. 56 and 57 illustrate a barrel-plunger locking arrangement to prevent withdrawal of the plunger, once the same is fully advanced relative to the barrel. In the embodiment illustrated in FIGS. 56 and 57, this locking arrangement takes the form of a pair of projecting locking tabs 560, 562 which have ramped leading or distal edges. These locking tabs are aligned with corresponding apertures in the side walls and finger flange 17 of the barrel 10, such that they can be deformed radially inwardly upon encountering and advancing through these apertures. Thereafter, the locking tabs 560 and 562 return to their original undeformed condition as shown in FIG. 57, whereby their trailing or proximal edges cannot thereafter be passed through the same apertures. That is, the radial extent of the apertures is less than that of the undeformed tabs 560 and 562.

Figure 60:
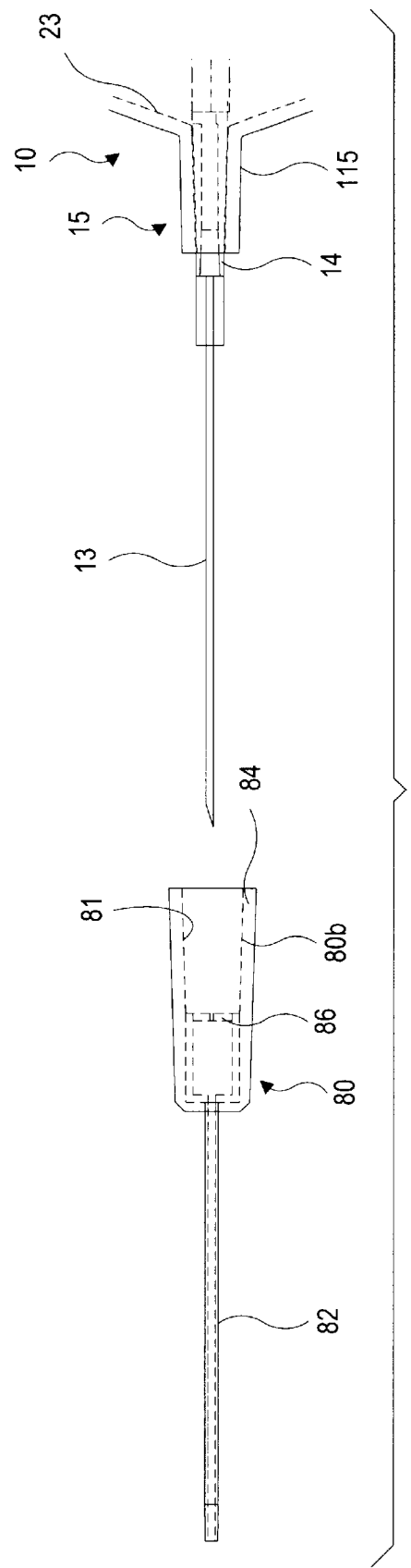
FIGS. 60 and 61 are elevations showing two forms of over-the-needle catheter which may be employed in connection with the needle and syringe assembly of the invention.

FIG. 60 depicts an over-the-needle ("OTN") catheter assembly including an OTN catheter 80 and the syringe assembly of FIGS. 1–20 (only a distal end portion of which is illustrated) with a hypodermic needle 13 mounted therein. In the embodiment of FIG. 60, the OTN catheter 80 is a polymeric catheter having an elongated tip 82 mounted thereto. Prior to use of the OTN catheter assembly, a proximal end surface 84 of the OTN catheter 80 is coaxially mounted over the nozzle 15 and the hypodermic needle 13 protrudes through both the nozzle 15 and the OTN catheter 80. The elongated tip 82 of the catheter 80 is advanced over the needle 13. Prior to use, i.e., prior to inserting the needle 13 and catheter tip 82 into a vein, the needle 13 and catheter tip 80 are enclosed by a removable cap (not shown).

Preferably, the catheter 80 includes an internal valve, such as a slit valve 86 to restrict the flow of fluids therethrough. Prior to and during normal use of the OTN catheter assembly, the OTN catheter 80 is held engaged over the nozzle 15 of the syringe assembly by locking luer tapers on the outer surface 115 of the nozzle 15 and the inner surface 81 of the catheter 80. Following puncture of the vein of a patient and insertion of the tip 82 of the OTN catheter 80 into the vein, the needle carrier 14 and the mounted needle 13 are retracted in the manner described above. At this retracted position the needle carrier 14 is irretrievably locked in place inside the barrel as described above. The syringe is then disengaged from the catheter by simultaneously rotating and withdrawing the syringe, so as to release the locking luer taper formed by surfaces 115 and 81, as shown in FIG. 50. The OTN catheter 80 is then advanced into the vein, and secured to the skin by adhesive tapes.

The purpose of the locking luer taper formed by surfaces 115 and 81 is to mechanically unify the syringe with the OTN catheter so that insertion force applied to the syringe is directly transmitted to the hypodermic needle 13 and catheter 80. Release of the locking luer taper disassociates this mechanical unity, permitting the syringe (with the needle 13 retracted) to be removed from the catheter 80.

During puncture of the vein, confirmation that the needle 13 and catheter tip 82 are located in the vein can be made by viewing blood entering the catheter 80 by capillary action. It, however, is also possible to confirm a flashback within the syringe barrel by partially retracting the plunger 11 relative to the barrel 10 to assure that continuity between the needle 13 and the vein is established. The side aperture 26 of the needle holder 14 opens into the flashback chamber thus created. Confirmation of proper insertion in the vein is indicated by blood entering the barrel chamber via the side aperture 26 in the needle holder 14.

To use the OTN catheter-syringe assembly, the skin of a patient is first prepared and a peripheral vein is made prominent. Under aseptic precautions the vein is punctured with the needle 13 and catheter tip 82, and the location of the needle tip is judged by the change in color under the catheter or by the appearance of blood in is the catheter or the flashback chamber. Once the location of the needle tip is confirmed, the needle carrier is retracted in the manner described above. While advancing and retaining the OTN catheter 80 in the vein, the syringe assembly is removed and an intravenous line is connected to the catheter 80. Finally, the catheter 80 is secured to the skin of the patient by adhesive tape.

Figure 61:
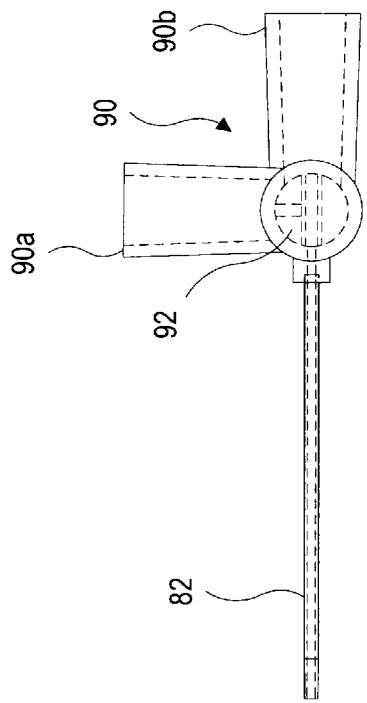

As shown in FIG. 61, it is possible to replace the OTN catheter 80 having the slit valve 86 with an OTN catheter assembly 90 having two orthogonally disposed body portions 90a and 90b, which are operatively coupled to the elongated catheter tip 82 by a rotary-type 3-way ball valve mechanism 92. The elongated catheter tip 82 is the same as that of the catheter 80 of FIGS. 24–26.

The various novel and improved syringe assemblies as described above offer a number of advantageous features, including but not limited to various combinations of the following:

The detents 34 in the plunger channel 33 add precision to the needle holder movement. For example, straight axial retraction of the needle in the plunger channel 33 avoids angulation of the needle and puncture of the barrel cavity. It does not require extending the overall length of the syringe, and avoids the need for special measures such as breaking the plunger to prevent re-use.

The proximal end part 16 of the barrel 10 is strengthened by reducing the circumference of the helical slot 19 (when used) from 360° to 270° or even further. Reinforcing rib 52 is also incorporated in the barrel for strength when using the helical slot. The rib 52 also acts as a track for the latching member 51.

The number of the components in the present invention is not significantly different from a conventional syringe to keep it cost effective.

Use of the sliding needle holder eliminates the usual needle holder on the barrel nozzle, which eliminates the associated dead-space and quantity of wasted medications left over in the syringe nozzle and the female needle holder.

The operation of the syringe is one-way so that accidental misuse is minimized, i.e., once retracted the needle holder is locked in place, so the needle cannot be re-extended.

Operation of the syringe is particularly safe because all the required manipulations of the various parts of the syringe are performed at or near the proximal end of the syringe, well away of the needle, during both the normal and retracting modes of operation.

The locking and disablement is automatic when the needle holder is retracted. Pull-back of the plunger is also blocked by the detent 75 in the plunger while the back-tracking of the needle holder in the helical slot is also blocked by the detent 75 when the needle holder with the lateral arm 32 is used.

In the rare event when only a partial dose of medicine is given to the patient, the syringe with leftover medicine can be rendered safe by retraction of the needle holder, while capping of the nozzle will prevent spillage.

It should be noted that the syringe assembly as described may be used to dispense medication or as a blood collection device. It may also be used to place an over-the-needle catheter, as described above.

While the present invention has been described with reference to one or more particular embodiments, those skilled in the art will recognize that many changes may be made thereto without departing from the spirit and scope of the present invention. Each of these embodiments and obvious variations thereof is contemplated as falling with the spirit and scope of the claimed invention, which is set forth in the following claims.

What is claimed is:

1. A safety syringe assembly, comprising:
   an elongated, generally cylindrical barrel having a hollow interior forming a hollow nozzle located at a distal end of said barrel and opening into the interior of said barrel,
   a plunger slidably mounted in said barrel and having a longitudinal open channel;
   a needle;
   a needle holder mounting said needle at a distal end thereof and slidably mounted in said longitudinal open channel of said plunger for movement between an advanced position in which said needle on the distal end of said needle holder projects from a distal end of said nozzle, and a retracted position in which said needle is retracted within said barrel;

a compression spring mounted inside of said barrel and means supporting a distal end portion of said spring against expansion; said spring urging said needle holder toward its retracted position; and a latch arrangement having a closed position in which said needle holder is latched relative to said barrel to hold said needle holder in its advanced position against the urging of said spring, and an open position in which said needle holder is unlatched relative to said barrel to allow said spring to expand in a proximal direction to move said needle holder to its retracted position; said latch arrangement including a radially projecting arm on one of said needle holder and said barrel by which the needle holder is directly or indirectly engaged with the barrel, at least when in its closed position.

2. The syringe assembly of claim 1 wherein said spring is a helical spring disposed around said plunger.

3. The syringe assembly of claim 1 wherein said spring is a helical spring disposed around said needle holder within said longitudinal open channel of said plunger.

4. The syringe assembly of claim 1 wherein said spring is a helical spring.

5. A safety syringe assembly, comprising:

an elongated, generally cylindrical barrel having a hollow interior forming a hollow nozzle located at a distal end of said barrel and opening into the interior of said barrel;

a plunger slidably mounted in said barrel and having a longitudinal open channel;

a needle holder slidably mounted in said longitudinal open channel of said plunger for movement between an advanced position in which a needle on the distal end of said needle holder projects from a distal end of said nozzle, and a retracted position in which said needle is retracted within said barrel;

a spring mounted inside said barrel and urging said needle holder toward its retracted position; and a latch having a closed position in which said needle holder is latched to said barrel to hold said needle holder in its advanced position against the urging of said spring, and an open position in which said needle holder is unlatched from said barrel to allow said spring to move said needle holder to its retracted position;

wherein said needle holder has a lateral arm which extends radially, and wherein said latch engages said lateral arm of said needle holder when said latch is in its closed position.

6. The syringe assembly of claim 1 wherein said barrel includes a guide slot and wherein said needle holder includes a lateral arm extending laterally from said plunger open channel into said guide, whereby said needle holder is guided by said guide slot as it moves toward its retracted position.

7. The syringe assembly of claim 6 wherein said latch is mounted for movement into and out of registry with a distal end of said guide slot for capturing and releasing said lateral arm at the distal end of said guide slot.

8. The syringe assembly of claim 1 which includes a hollow needle attached to the distal end of said needle holder.

9. The syringe assembly of claim 5 wherein said spring comprises a helical spring disposed around said plunger.

10. A safety syringe assembly comprising:

an elongated, generally cylindrical barrel having a hollow interior forming a hollow nozzle located at a distal end of said barrel and opening into the interior of said barrel;

a plunger slidably mounted in said barrel and having a longitudinal open channel;

a needle holder slidably mounted in said longitudinal open channel of said plunger for movement between an advanced position in which a needle on the distal end of said needle holder projects from a distal end of said nozzle, and a retracted position in which said needle is retracted within said barrel;

a spring mounted inside said barrel and urging said needle holder toward its retracted position; and a latch having a closed position in which said needle holder is latched to said barrel to hold said needle holder in its advanced position against the urging of said spring, and an open position in which said needle holder is unlatched from said barrel to allow said spring to move said needle holder to its retracted position;

wherein said latch comprises a needle holder locking element rotatably mounted on said barrel for rotary movement between a locking position and non-locking position on the barrel.

11. The syringe assembly of claim 1 wherein said barrel has outwardly extending gripping flanges and said latch comprises a needle holder locking element mounted on one of said barrel flanges for movement between a locking position and non-locking position.

12. The syringe assembly of claim 6 wherein said guide slot is formed in the wall of said barrel and extends radially through the wall of said barrel.

13. The syringe assembly of claim 6 wherein said guide slot includes a detent at a proximal end thereof for resisting advancing movement of said needle holder after it has been fully retracted.

14. The syringe assembly of claim 1 wherein said longitudinal open channel of said plunger includes a detent for slidably retaining said needle holder within said longitudinal channel.

15. The syringe assembly of claim 1 wherein said barrel includes an outwardly extending finger flange to facilitate gripping of the barrel, and wherein said flange can be used to rotate the barrel relative to the plunger in a direction for releasing said latch to effect one-handed rotary retraction of the needle holder.

16. The syringe assembly of claim 15 wherein said lateral arm extends radially through the barrel wall, and wherein said latch is located adjacent said flange to engage a portion of said lateral arm.

17. The syringe assembly of claim 1 wherein said latch is formed on said needle holder and releasably engages said barrel.

18. The syringe assembly of claim 1 and further including a retaining member comprising said means for supporting a distal end portion of the spring.

19. The syringe assembly of claim 18 and further including an inwardly extending surface on said barrel supporting said retaining member.

20. The syringe assembly of claim 6 wherein said latch is located at a distal end of said guide slot, and comprises a longitudinal track on an outer surface of said barrel and a locking element slidably mounted on said track for reciprocating movement between a locking position at said distal end of said guide slot and a non-locking position away from said distal end of said guide slot.

21. The syringe assembly of claim 1 wherein said latch comprises a locking element formed as an integral part of the outer surface of said barrel and including an integral hinge permitting pivoting movement of said locking element between a locking position and a non-locking position.

22. A syringe assembly, comprising:
- an elongated, generally cylindrical barrel having a hollow interior forming a hollow nozzle located at a distal end of said barrel and opening into the interior of said barrel;
- a plunger slidably mounted in said barrel and having a longitudinal open channel;
- a needle holder slidably mounted in said longitudinal open channel of said plunger;
- a latch arrangement for latching and unlatching said needle holder relative to said barrel; said latch arrangement including a radially projecting arm on one of said needle holder and said barrel by which the needle holder is directly or indirectly engaged with the barrel, at least when latching said needle holder relative to said barrel; and
- a compression spring located in said barrel in surrounding relation to said needle holder and having a distal end held against expansion so as to expand in a proximal direction for retracting said needle holder in response to unlatching said needle holder by said latching means.

23. The syringe assembly of claim 22 wherein said spring comprises a coil spring disposed around said plunger.

24. The syringe assembly of claim 22 wherein said spring comprises a coil spring disposed around said needle holder within said longitudinal open channel of said plunger.

25. The syringe assembly of claim 22 wherein said spring comprises a coil spring, and further including a support member for supporting a distal end of said coil spring.

26. The syringe assembly of claim 25 wherein the support member comprises an L-shaped bracket supported by a proximal portion of said barrel.

27. A syringe assembly, comprising:
- an elongated, generally cylindrical barrel having a hollow interior forming a hollow nozzle located at a distal end of said barrel and opening into the interior of said barrel;
- a plunger slidably mounted in said barrel and having a longitudinal open channel;
- a needle holder slidably mounted in said longitudinal open channel of said plunger;
- a latch for latching and unlatching said needle holder relative to said barrel; and
- a spring for retracting said needle holder in response to unlatching said needle holder by said latching means;
- wherein said needle holder has a lateral arm which extends radially, and wherein said latch releasably engages the lateral arm of said needle holder.

28. The syringe assembly of claim 27 wherein said latch comprises a needle holder locking element rotatably mounted on said barrel for rotary movement between a locking position and non-locking position relative to said lateral arm.

29. The syringe assembly of claim 22 wherein said barrel includes outwardly extending gripping flanges and said latch comprises a locking element mounted on one of said barrel flanges for movement between a locking position and non-locking position relative to said needle holder.

30. The syringe assembly of claim 27 wherein a guide slot is formed in a proximal wall portion of said barrel for receiving and guiding said lateral arm.

31. The syringe assembly of claim 30 wherein said guide slot includes a detent at a proximal end thereof for resisting advancing movement of said needle holder after it has been fully retracted.

32. The syringe assembly of claim 21 wherein said longitudinal open channel of said plunger includes a detent for slidably retaining said needle holder within said longitudinal open channel.

33. The syringe assembly of claim 30 wherein said barrel includes outwardly extending finger flanges to facilitate gripping of the barrel, and wherein said flanges can be used to rotate the barrel relative to the plunger in a direction for releasing said latch to effect one-handed rotary retraction of the needle holder.

34. The syringe assembly of claim 33 wherein said lateral arm extends radially through the barrel wall.

35. The syringe assembly of claim 34 wherein said latch is located adjacent said flange to releasably engage a portion of said needle holder lateral arm.

36. The syringe assembly of claim 30 wherein said needle holder includes a lateral arm for engaging the latch and said barrel has an open end and said plunger includes recesses alignable with said open end of said barrel for defining a relief space for deformation of said open end of barrel to permit initial insertion of said lateral arm of said needle holder past said open end of said barrel and into said guide slot.

37. The syringe assembly of claim 22 and further including a support element to support the spring at a distal end portion of the spring.

38. The syringe assembly of claim 23 and further an inwardly extending surface on said barrel which supports a distal end of the spring.

39. The syringe assembly of claim 30 wherein said latch comprises a longitudinal track on an outer surface of said barrel and a locking element slidably mounted on said track for reciprocating movement between a locking position at a distal end of said guide slot and a non-locking position away from said distal end of said guide slot.

40. The syringe assembly of claim 22 wherein said latch comprises a locking element formed as an integral part of the outer surface of said barrel and including an integral hinge for permitting pivoting movement of said locking element between a locking position and a non-locking position.

41. The syringe assembly of claim 22 wherein the barrel and plunger have cooperating interlocking elements which engage and lock when the plunger is fully advanced relative to the barrel, to prevent retraction of the plunger.

42. An over-the-needle catheter and syringe assembly, comprising:
- an elongated, generally cylindrical barrel having a hollow interior forming a hollow nozzle located at a distal end of said barrel and opening into the interior of said barrel;
- a plunger slidably mounted in said barrel and having a longitudinal open channel;
- a needle holder slidably mounted in said longitudinal open channel of said plunger for movement between an advanced position in which a needle on the distal end of said needle holder projects from a distal end of said nozzle, and a retracted position in which said needle is retracted within said barrel;
- an elastic biasing member mounted inside said barrel and contacting said needle holder for urging said needle holder toward its retracted position;
- a latch releasably engageable with said needle holder and movable between a closed position in which said needle holder is latched to hold said needle holder in its advanced position against the urging of said biasing means, and an open position in which said needle holder is unlatched to allow said biasing means to move said needle holder to its retracted position;

an over-the-needle catheter; and cooperating locking surfaces on said catheter and said syringe releasably securing said catheter to said syringe.

43. The catheter and syringe assembly of claim 42 wherein said cooperating locking surfaces include a luer taper located on said nozzle which engages with a mating luer tape located on said catheter.

44. The catheter and syringe assembly of claim 42 said catheter further including a valve.

45. The catheter and syringe assembly of claim 44 wherein said valve comprises a slit valve.

46. The catheter and syringe assembly of claim 44 wherein said valve comprises a rotary ball valve.

47. The catheter and syringe assembly of claim 42 wherein said catheter comprises a catheter body, and an elongated, generally cylindrical catheter tip extending from said body.

48. The catheter and syringe assembly of claim 47 and further including a slit valve in said catheter body.

49. The catheter and syringe assembly of claim 42 wherein said catheter comprises a pair of orthogonally disposed catheter body portions, an elongated projecting catheter tip aligned with one of said body portions and a valve for operatively coupling said catheter body portions with said tip.

50. The catheter and syringe assembly of claim 49 wherein said valve comprises a rotary ball valve.

51. A syringe assembly comprising:

an elongated, generally cylindrical barrel forming a hollow nozzle located at the distal end of said barrel and opening into the interior of said barrel;

a plunger slidably mounted in the said barrel and forming a longitudinal channel;

a needle holder slidably mounted in said longitudinal open channel of the said plunger and having a lateral arm;

latching means for latching and unlatching said lateral arm of said needle holder with the needle holder distally advanced relative to the barrel; and elastic means located in said barrel for retracting said needle holder within the barrel in response to the unlatching of the needle holder from said barrel.

52. The syringe assembly of claim 51 and further including guide means forming a guide slot extending along a proximal end portion of said barrel for engaging said lateral arm of said needle holder.

53. The syringe assembly of claim 51 and further including guide means forming a helical guide slot extending along a proximal end portion of said barrel for engaging said lateral arm of said needle holder.

54. The syringe assembly of claim 51 wherein said latching means comprises a needle holder locking element slidably mounted on said barrel for reciprocating movement between a locking position and a non-locking position.

55. The syringe assembly of claim 51 wherein the barrel and plunger have cooperating interlocking elements which engage and lock when the plunger is fully advanced relative to the barrel, to prevent retraction of the plunger.

56. A syringe assembly comprising:

an elongated, generally cylindrical barrel forming a hollow nozzle located at the distal end of said barrel and opening into the interior of said barrel;

a plunger slidably mounted in the said barrel and forming a longitudinal open channel;

a needle holder slidably mounted in said longitudinal open channel of the said plunger and having a lateral arm;

latching means for latching and unlatching said lateral arm of said needle holder relative to the barrel; and elastic means located in the proximal end portion of said barrel and responsive to unlatching of the needle holder from said barrel for retracting said needle holder within the barrel.

57. The syringe assembly of claim 56 wherein the barrel includes an outwardly extending finger flange, and said latching means include a movable lever in the flange to capture the lateral arm of said needle holder that extends adjacent to the flange.

58. The syringe assembly of claim 56 which includes a hollow needle attached to the distal end of said needle holder.

59. The syringe assembly of claim 56 wherein a guide slot is formed in the wall of the barrel and extends radially through the wall of the barrel.

60. The syringe assembly of claim 56 wherein the elastic means comprises a spring and a proximal portion of the barrel has an internally projecting surface for directly or indirectly supporting a distal end of said spring.

61. The syringe assembly of claim 56 wherein the elastic means comprises a spring and a bracket at a proximal end portion of the barrel supports a distal end of the spring.

62. The syringe assembly of claim 56 wherein the proximal portion of the barrel containing the elastic retraction means has a larger inside diameter than the distal portion of the barrel to define said projecting surface at a shoulder formed at the transition between the proximal and distal barrel portions.

63. The syringe assembly of claim 1, wherein said channel of said plunger has a locking detent that holds the needle holder at the proximal end of the plunger when retracted.

64. The syringe assembly of claim 22, wherein said channel of said plunger has a locking detent that holds the needle holder at the proximal end of the plunger when retracted.

65. The syringe assembly of claim 51, wherein said channel of said plunger has locking detent means that hold the needle holder at the proximal end of the plunger when retracted.

66. The syringe assembly of claim 56, wherein said channel of said plunger has locking detent means that hold the needle holder at the proximal end of the plunger when retracted.

67. A syringe assembly, comprising:

an elongated generally cylindrical barrel forming a hollow nozzle located at a distal end of said barrel and opening into the interior of said barrel;

a plunger slidably mounted in said barrel and forming a longitudinal open channel;

a needle holder slidably mounted in said longitudinal open channel of said plunger;

a latch that releasably couples the needle holder with the barrel; and an elastic spring located in a proximal end portion of said barrel for retracting said needle holder within the open channel in response to release of said latch.

68. The syringe assembly of claim 67 wherein said barrel includes an internally projecting support ring for seating one of the elastic spring and a support element for supporting said elastic spring, said elastic spring being compressed by the needle holder when the needle holder is coupled to the barrel by the latch.

69. The syringe assembly of claim 67 including a bracket projecting into said barrel for supporting a distal end of said elastic spring, said elastic spring being compressed when the latch is unreleased and expanding to its full uncompressed length when the latch is released.

70. The syringe assembly of claim 67 wherein said barrel includes a finger flange to facilitate gripping of the barrel and said latch comprises a sliding lever mounted to said finger flange and removably projecting into the plunger open channel to releasably latch the needle holder to the barrel.

71. The syringe assembly of claim 67 wherein said latch comprises a needle holder locking element slidably mounted on said barrel for reciprocating movement between a locking position and non-locking position.

72. The syringe assembly of claim 67 wherein said nozzle has a male luer taper on an outer surface thereof.

73. The syringe assembly of claim 52 wherein said longitudinal open channel and said guide slot have detents for retaining said needle holder lateral arm at a proximal end thereof when said needle holder is retracted to thereby render the syringe assembly interlocked and inoperative.

74. The needle-syringe assembly of claim 67 wherein said plunger open channel includes a plurality of detent elements formed as integral parts of an interior surface of said open channel for retaining the needle holder in sliding engagement with said open channel.

75. A syringe assembly, comprising:
an elongated, generally cylindrical barrel having a hollow interior forming a hollow nozzle located at a distal end of said barrel and opening into the interior of said barrel;
a plunger slidably mounted in said barrel and forming a longitudinal open channel;
a needle holder slidably mounted in said longitudinal open channel of said plunger;
guide slot means defining a guide slot extending along a proximal end portion of said barrel for guiding a retracting motion of said needle holder within the barrel in response to a retractile force between the barrel and the needle holder; and
latching means on said barrel for latching and unlatching said needle holder at the distal end of said guide slot.

76. The syringe assembly of claim 75 wherein said guide slot has latching means at a distal end thereof for releasably latching said needle holder against said retractable force, and detent means for interlocking the barrel, plunger and needle holder at a proximal end.

77. A syringe assembly, of claim 75 including latching means on said barrel for releasably latching said needle holder against said retractable force, and comprising a locking element formed as an integral part of the outer surface of said barrel and including an integral hinge for permitting pivoting movement of said locking element between a locking position, and a non-locking position.

78. A syringe assembly, comprising:
an elongated, generally cylindrical barrel having a hollow interior forming a hollow nozzle located at a distal end of said barrel and opening into the interior of said barrel;
a plunger slidably mounted in said barrel and forming a longitudinal open channel;
a needle holder slidably mounted in said longitudinal open channel of said plunger and having a lateral arm;
means defining a guide slot extending along a proximal end portion of said barrel for engaging said lateral arm of needle holder and guiding said needle holder within the barrel in response to relative movement between the barrel and the needle holder;
latching means on said barrel for latching and unlatching said needle holder at a distal end of said guide slot, and comprising a locking tab hingedly joined to said barrel and movable between a locking position in engagement with said lateral arm of said needle holder at said distal end of said guide slot and a non-locking position out of engagement with said lateral arm of said needle holder; and
retractable force providing means coupled with said needle holder for applying a force thereto for causing said relative movement between said barrel and said needle holder in a direction for retracting said needle holder within said barrel.

79. The syringe assembly of claim 78 wherein the retractable force providing means is a coil spring.

80. A method of assembling a safety syringe assembly comprising, in sequence:
providing a barrel, a plunger having a longitudinal open channel, a needle holder which mounts a needle at a distal end thereof, a plunger cap, and a helical coil compression spring;
axially inserting a plunger cap and said needle holder with said compression spring thereabout into said barrel;
aligning said channel portion of said plunger with said needle holder;
axially inserting said plunger into the barrel; and
applying longitudinal force on said plunger for causing said plunger to advance into said barrel and cause latching of said needle holder to said barrel and sliding engagement of said needle holder with said plunger channel.

81. The method of syringe assembly of claim 80 wherein said needle holder includes a lateral arm for engaging a guide slot in said barrel and said barrel has an open end and said plunger includes recesses alignable with said open end of said barrel for defining a relief space for deformation of said open end of barrel to permit initial insertion of said lateral arm of said needle holder past said open end of said barrel into said guide slot, and further including deforming said open end of said barrel and simultaneously inserting said lateral arm of said needle holder past said open end of said barrel and into said guide slot.

82. A syringe assembly, comprising:
an elongated, generally cylindrical barrel having a hollow interior forming a hollow nozzle located at a distal end of said barrel and opening into the interior of said barrel;
a plunger slidably mounted in said barrel and having a longitudinal open channel;
a needle holder slidably mounted in said longitudinal open channel of said plunger for movement between an advanced position in which a needle on the distal end of said needle holder projects from a distal end of said nozzle, and a retracted position in which said needle is retracted within said barrel;
an elastic biasing member mounted inside said barrel and contacting said needle holder for urging said needle holder toward its retracted position; and
a latch releasably engageable with said needle holder and movable between a closed position in which said needle holder is latched to hold said needle holder in its advanced position against the urging of said biasing means, and an open position in which said needle holder is unlatched to allow said biasing means to move said needle holder to its retractable position.

83. A syringe assembly, comprising:

an elongated, generally cylindrical barrel having a hollow interior forming a hollow nozzle located at a distal end of said barrel and opening into the interior of said barrel;

a plunger slidably mounted in said barrel and forming a longitudinal open channel;

a needle holder slidably mounted in said longitudinal open channel of said plunger;

retracting means for retracting said needle holder relative to the open channel in response to a retractile force between the barrel and the needle holder; and latching means on said barrel for latching and unlatching said needle holder.

84. A syringe assembly, comprising:

an elongated, generally cylindrical barrel having a hollow interior forming a hollow nozzle located at a distal end of said barrel and opening into the interior of said barrel;

a plunger slidably mounted in said barrel and forming a longitudinal open channel;

a needle holder slidable mounted in said longitudinal open channel of said plunger and having a lateral arm;

a guide slot in said barrel for engaging said lateral arm of needle holder and guiding said needle holder within the barrel in response to relative movement between the barrel and the needle holder;

latching means on said barrel for latching and unlatching said needle holder; and retractable force providing means coupled with said needle holder for applying a force thereto for causing said relative movement between said barrel and said needle holder in a direction for retracting said needle holder.

* * * * *

UNITED STATES PATENT AND TRADEMARK OFFICE
CERTIFICATE OF CORRECTION

PATENT NO. : 6,156,013
DATED : December 5, 2000
INVENTOR(S) : Sakharam D. Mahurkar It is certified that error appears in the above-identified patent and that said Letters Patent is hereby corrected as shown below:

Column 16, claim 1,
Line 56, please replace "," with -- ; --.

Column 17, claim 6,
Line 51, please insert -- slot -- between "guide" and ",".

Signed and Sealed this

Second Day of October, 2001

Attest:

NICHOLAS P. GODICI
*Attesting Officer*   *Acting Director of the United States Patent and Trademark Office*